(12) United States Patent
Barabas et al.

(10) Patent No.: US 11,441,132 B2
(45) Date of Patent: Sep. 13, 2022

(54) MUTATED SLEEPING BEAUTY TRANSPOSASE

(71) Applicant: European Molecular Biology Laboratory, Heidelberg (DE)

(72) Inventors: Orsolya Barabas, Gaiberg (DE); Irma Querques, Zurich (CH); Cecilia Ines Zuliani, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 0 days.

(21) Appl. No.: 16/640,976

(22) PCT Filed: Aug. 17, 2018

(86) PCT No.: PCT/EP2018/072320
§ 371 (c)(1),
(2) Date: Feb. 21, 2020

(87) PCT Pub. No.: WO2019/038197
PCT Pub. Date: Feb. 28, 2019

(65) Prior Publication Data
US 2021/0123031 A1    Apr. 29, 2021

(30) Foreign Application Priority Data
Aug. 21, 2017  (EP) .................................. 17187128

(51) Int. Cl.
*C12N 9/12* (2006.01)
(52) U.S. Cl.
CPC .................. *C12N 9/1241* (2013.01)
(58) Field of Classification Search
None
See application file for complete search history.

(56) References Cited

U.S. PATENT DOCUMENTS

| 2005/0003542 A1* | 1/2005 | Kay | C12N 15/902 |
| | | | 435/455 |
| 2017/0226531 A1* | 8/2017 | Craig | C12N 9/1241 |
| 2018/0051265 A1* | 2/2018 | Cooper | A61P 31/04 |

FOREIGN PATENT DOCUMENTS

EP    2025748 A1    2/2009

OTHER PUBLICATIONS

Chica et al. Curr Opin Biotechnol. Aug. 2005;16(4):378-84. (Year: 2006).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Cui et al. J Mol Biol. May 17, 2002;318(5):1221-35 (Year: 2002).*
Grabundzija et al. Nucleic Acids Res. Feb. 1, 2013;41(3):1829-47 (Year: 2013).*
Alignment of Seq ID No. 7 of US20180051265 to Seq ID No. 2 (Year: 2018).*
Geurts et al.., "Gene transfer into genomes of human cells by the sleeping beauty transposon system", Molecular Therapy, Academic Press, US, vol. 8, No. 1, pp. 108-117, Jul. 1, 2003.
Fletcher et al., "Enhanced Transposition Activities of Mutant Sleeping Beauty Transposases", Molecular Therapy, vol. 9, No. 1, pp. 178-179, May 1, 2004.
"Amphibians transposase sequence, Seq ID 31.", XP002776513, retrieved from EBI accession No. CSP: AXV14499 Database accession No. AXV14499, Apr. 1, 2010 (1 page).
"Hypophthalmichthys molitrix Thm3 transposase, Seq ID 24.", XP002776514, retrieved from EBI accession No. GSP: BBF14943 Database accession No. BBF14943 sequence.
International Search Report and Written Opinion, International Patent Application No. PCT/EP2018/072320, dated Oct. 4, 2018 (16 pages).

* cited by examiner

*Primary Examiner* — Christian L Fronda
(74) *Attorney, Agent, or Firm* — Hamre, Schumann, Mueller & Larson, P.C.

(57) ABSTRACT

The present invention relates to improved transposase polypeptides having increased solubility. The enzyme of the invention was developed based on the Sleeping Beauty (SB) transposase. The invention provides further nucleic acids, vectors and recombinant cells encoding or containing the improved transposase, as well as a transposase system. Furthermore provided are medical and non-medical uses of the transposase of the invention for gene delivery. The invention is in particular useful as a tool for gene delivery in genetically modified cell based therapeutic approaches for treating various diseases.

9 Claims, 20 Drawing Sheets

Specification includes a Sequence Listing.

Figure 1:
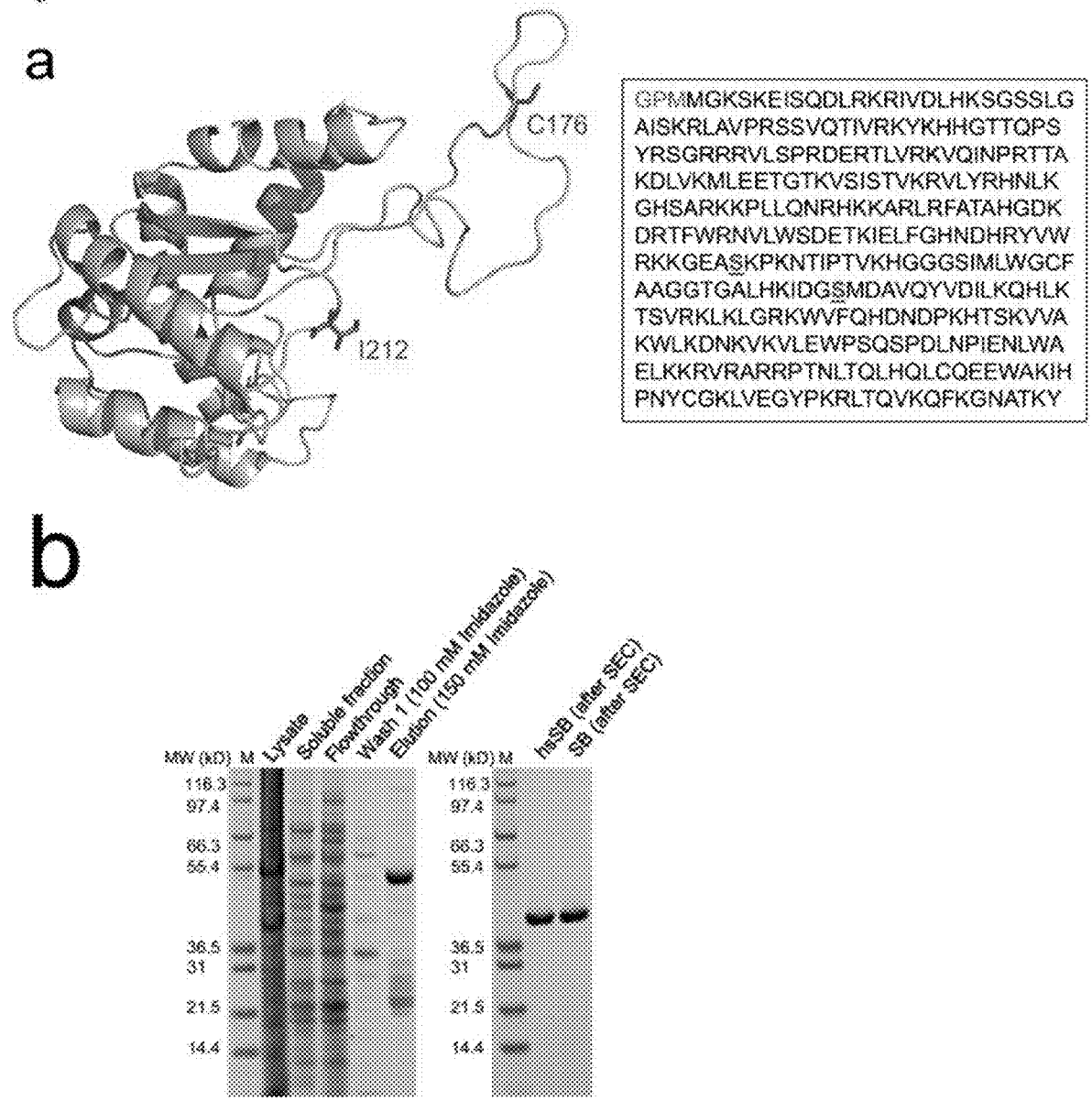
Figure 1:
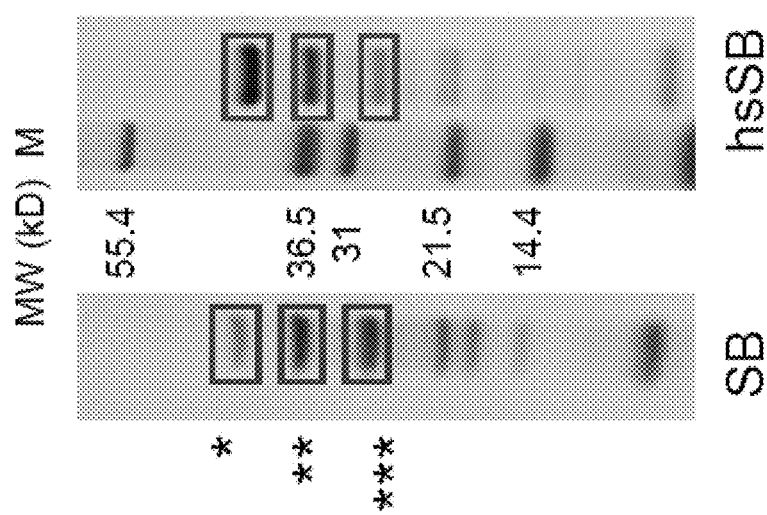

Figure 1 cont.:
c
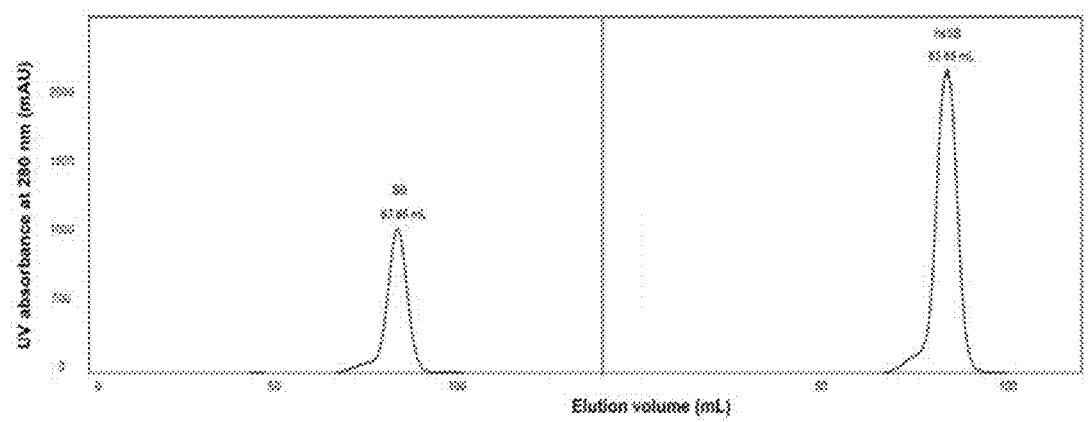
d
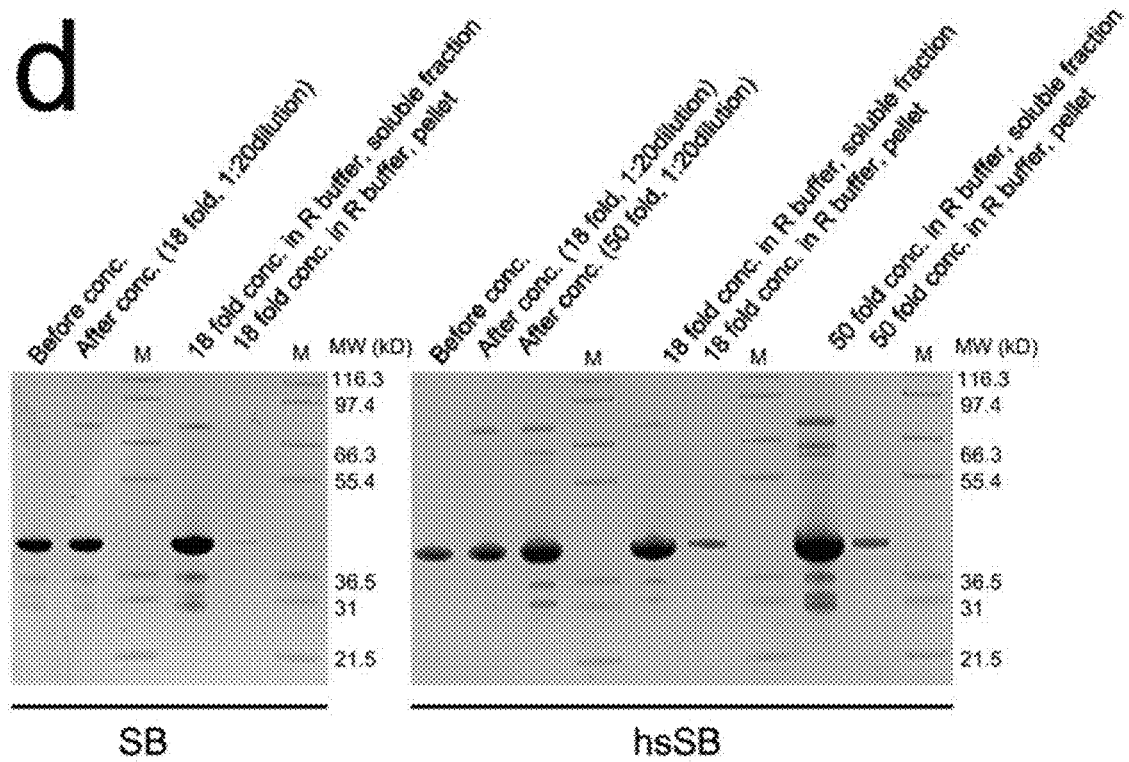

Figure 1 cont.:
e
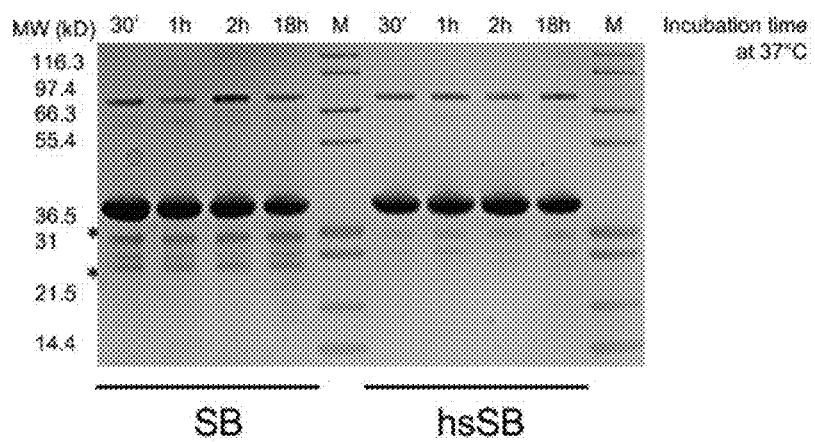
f
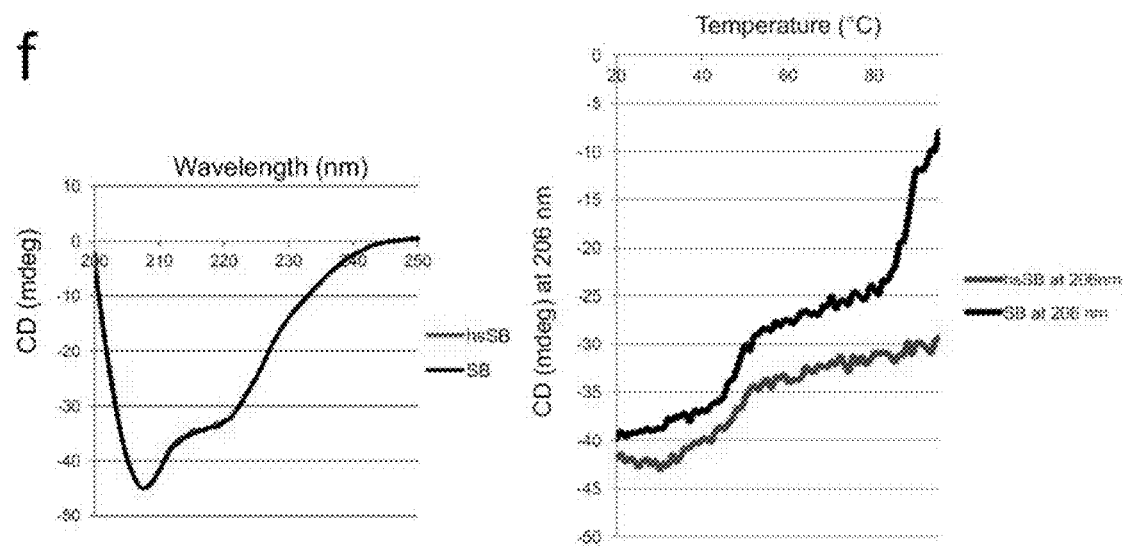

Figure 4:

| Single insertions sequence | Chromosome |
|---|---|
| tgtatatatataTACAGTTGAAGTC | 1 |
| gacacatacaacaTACAGTTGAAGTC | 9 |
| ctgttggatgcatcTACAGTTGAAGTC | 7 |
| gatatatacatatgTACAGTTGAAGTC | 17 |
| gtacgagtgtatgTACAGTTGAAGTC | 9 |
| cttcaggaacaaaTACAGTTGAAGTC | 17 |
| tcaactttcagaaatgTACAGTTGAAGTC | 1 |
| ggaccatacataacaTACAGTTGAAGTC | 9 |
| gtactgagtgtatgTACAGTTGAAGTC | 9 |
| tttcaggaacaaaTACAGTTGAAGTC | 17 |
| actctcctatgataTACAGTTGAAGTC | 2 |
| actctcctatgataTACAGTTGAAGTC | 2 |
| aataatgctcagttaTACAGTTGAAGTC | 19 |
| atggcagttaacaTACAGTTGAAGTC | 12 |
| tattccatgcataTACAGTTGAAGTC | 6 |
| tatagctaacaataTACAGTTGAAGTC | 1 |
| gcaagtcctgtcaTACAGTTGAAGTC | 12 |
| ttaaatgaataaTACAGTTGAAGTC | 12 |
| gacacatacaatcaTACAGTTGAAGTC | 9 |
| aaagcaatagcacaTACAGTTGAAGTC | 17 |
| ttgtataaatcataTACAGTTGAAGTC | 8 |
| tatagctaacaataTACAGTTGAAGTC | 1 |
| cctaatcatctactTACAGTTGAAGTC | 1 |
| ttgtataaatcataTACAGTTGAAGTC | 8 |
| catgtcacatgaagTACAGTTGAAGTC | 5 |
| agtgaggtttaacaTACAGTTGAAGTC | 22 |
| ctatttggaaacaTACAGTTGAAGTC | 1 |

| Double insertions sequence | Chromosome |
|---|---|
| catgtcacatgaagTACAGTTGAAGTC——GACTTCAACTGTAcattaggtaaccac | 5 |
| attgtataaatcataTACAGTTGAAGTC——GACTTCAACTGTAtcacatattcata | 6 |
| tctttgttgcataTACAGTTGAAGTC——GACTTCAACTGTAgtatgcattctg | 13 |
| ccctcctacacaTACAGTTGAAGTC——GACTTCAACTGTAcatatactactaa | X | red = left IR
blue = right IR a

C

Figure 10:

| hsSB protein (μg) | 0 | 5 | 10 | 20 |
|---|---|---|---|---|
| HeLa cells | 0 ± 0 | 38.5 ± 9 | 42 ± 1.4 | 45 ± 5.7 |
| CHO cells | 0 ± 0 | 39.5 ± 6.4 | 50.5 ± 4.9 | 73 ± 0 |
| mESCs | 0 ± 0 | 4 ± 0 | 10 ± 7.1 | 18 ± 1.4 |

Venus+ cells 21 days after electroporation (%)

SEQUENCE LISTING

```
<160> NUMBER OF SEQ ID NOS: 34

<210> SEQ ID NO 1
<211> LENGTH: 340
<212> TYPE: PRT
<213> ORGANISM: artificial
<220> FEATURE:
<223> OTHER INFORMATION: hsSB

<400> SEQUENCE: 1

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
                20                  25                  30

Ala Val Pro Arg Ser Ser Val Gln Thr Ile Val Arg Lys Tyr Lys His
            35                  40                  45

His Gly Thr Thr Gln Pro Ser Tyr Arg Ser Gly Arg Arg Arg Val Leu
        50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly His Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
        130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Ser
                165                 170                 175

Lys Pro Lys Asn Thr Ile Pro Thr Val Lys His Gly Gly Gly Ser Ile
                180                 185                 190

Met Leu Trp Gly Cys Phe Ala Ala Gly Gly Thr Gly Ala Leu His Lys
            195                 200                 205

Ile Asp Gly Ser Met Asp Ala Val Gln Tyr Val Asp Ile Leu Lys Gln
```

```
                  210                 215                 220
His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                    245                 250                 255

Trp Leu Lys Asp Asn Lys Val Lys Val Leu Glu Trp Pro Ser Gln Ser
                260                 265                 270

Pro Asp Leu Asn Pro Ile Glu Asn Leu Trp Ala Glu Leu Lys Lys Arg
                275                 280                 285

Val Arg Ala Arg Arg Pro Thr Asn Leu Thr Gln Leu His Gln Leu Cys
290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 2
<211> LENGTH: 340
<212> TYPE: PRT
<213> ORGANISM: artificial
<220> FEATURE:
<223> OTHER INFORMATION: non mutated SB100X

<400> SEQUENCE: 2

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
                20                  25                  30

Ala Val Pro Arg Ser Ser Val Gln Thr Ile Val Arg Lys Tyr Lys His
                35                  40                  45

His Gly Thr Thr Gln Pro Ser Tyr Arg Ser Gly Arg Arg Arg Val Leu
            50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly His Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Gly Glu Ala Cys
                165                 170                 175

Lys Pro Lys Asn Thr Ile Pro Thr Val Lys His Gly Gly Gly Ser Ile
                180                 185                 190

Met Leu Trp Gly Cys Phe Ala Ala Gly Gly Thr Gly Ala Leu His Lys
            195                 200                 205

Ile Asp Gly Ile Met Asp Ala Val Gln Tyr Val Asp Ile Leu Lys Gln
210                 215                 220

His Leu Lys Thr Ser Val Arg Lys Leu Lys Leu Gly Arg Lys Trp Val
```

```
                225                 230                 235                 240

Phe Gln His Asp Asn Asp Pro Lys His Thr Ser Lys Val Val Ala Lys
                        245                 250                 255

Trp Leu Lys Asp Asn Lys Val Lys Val Leu Glu Trp Pro Ser Gln Ser
                        260                 265                 270

Pro Asp Leu Asn Pro Ile Glu Asn Leu Trp Ala Glu Leu Lys Lys Arg
                        275                 280                 285

Val Arg Ala Arg Arg Pro Thr Asn Leu Thr Gln Leu His Gln Leu Cys
                    290                 295                 300

Gln Glu Glu Trp Ala Lys Ile His Pro Asn Tyr Cys Gly Lys Leu Val
        305                 310                 315                 320

Glu Gly Tyr Pro Lys Arg Leu Thr Gln Val Lys Gln Phe Lys Gly Asn
                        325                 330                 335

Ala Thr Lys Tyr
                    340

<210> SEQ ID NO 3
<211> LENGTH: 343
<212> TYPE: PRT
<213> ORGANISM: artificial
<220> FEATURE:
<223> OTHER INFORMATION: hsSB for recombinant expression

<400> SEQUENCE: 3

Gly Pro Met Met Gly Lys Ser Lys Glu Ile Ser Gln Asp Leu Arg Lys
        1               5                   10                  15

Arg Ile Val Asp Leu His Lys Ser Gly Ser Ser Leu Gly Ala Ile Ser
                        20                  25                  30

Lys Arg Leu Ala Val Pro Arg Ser Ser Val Gln Thr Ile Val Arg Lys
                    35                  40                  45

Tyr Lys His His Gly Thr Thr Gln Pro Ser Tyr Arg Ser Gly Arg Arg
                50                  55                  60

Arg Val Leu Ser Pro Arg Asp Glu Arg Thr Leu Val Arg Lys Val Gln
        65                  70                  75                  80

Ile Asn Pro Arg Thr Thr Ala Lys Asp Leu Val Lys Met Leu Glu Glu
                        85                  90                  95

Thr Gly Thr Lys Val Ser Ile Ser Thr Val Lys Arg Val Leu Tyr Arg
                    100                 105                 110

His Asn Leu Lys Gly His Ser Ala Arg Lys Pro Leu Leu Gln Asn
                115                 120                 125

Arg His Lys Lys Ala Arg Leu Arg Phe Ala Thr Ala His Gly Asp Lys
                    130                 135                 140

Asp Arg Thr Phe Trp Arg Asn Val Leu Trp Ser Asp Glu Thr Lys Ile
        145                 150                 155                 160

Glu Leu Phe Gly His Asn Asp His Arg Tyr Val Trp Arg Lys Lys Gly
                        165                 170                 175

Glu Ala Ser Lys Pro Lys Asn Thr Ile Pro Thr Val Lys His Gly Gly
                    180                 185                 190

Gly Ser Ile Met Leu Trp Gly Cys Phe Ala Ala Gly Gly Thr Gly Ala
                195                 200                 205

Leu His Lys Ile Asp Gly Ser Met Asp Ala Val Gln Tyr Val Asp Ile
                    210                 215                 220

Leu Lys Gln His Leu Lys Thr Ser Val Arg Lys Leu Lys Leu Gly Arg
        225                 230                 235                 240

Lys Trp Val Phe Gln His Asp Asn Asp Pro Lys His Thr Ser Lys Val
```

```
                    245                 250                 255
Val Ala Lys Trp Leu Lys Asp Asn Lys Val Lys Val Leu Glu Trp Pro
            260                 265                 270

Ser Gln Ser Pro Asp Leu Asn Pro Ile Glu Asn Leu Trp Ala Glu Leu
        275                 280                 285

Lys Lys Arg Val Arg Ala Arg Arg Pro Thr Asn Leu Thr Gln Leu His
    290                 295                 300

Gln Leu Cys Gln Glu Glu Trp Ala Lys Ile His Pro Asn Tyr Cys Gly
305                 310                 315                 320

Lys Leu Val Glu Gly Tyr Pro Lys Arg Leu Thr Gln Val Lys Gln Phe
                325                 330                 335

Lys Gly Asn Ala Thr Lys Tyr
            340
```

<210> SEQ ID NO 4
<211> LENGTH: 27
<212> TYPE: DNA
<213> ORGANISM: Homo sapiens

<400> SEQUENCE: 4
tgtatatata tatatacagt tgaagtc                                27

<210> SEQ ID NO 5
<211> LENGTH: 27
<212> TYPE: DNA
<213> ORGANISM: Homo sapiens

<400> SEQUENCE: 5
gacacataca tacatacagt tgaagtc                                27

<210> SEQ ID NO 6
<211> LENGTH: 27
<212> TYPE: DNA
<213> ORGANISM: Homo sapiens

<400> SEQUENCE: 6
ctgttggatg cctctacagt tgaagtc                                27

<210> SEQ ID NO 7
<211> LENGTH: 27
<212> TYPE: DNA
<213> ORGANISM: Homo sapiens

<400> SEQUENCE: 7
gatatataca tatgtacagt tgaagtc                                27

<210> SEQ ID NO 8
<211> LENGTH: 27
<212> TYPE: DNA
<213> ORGANISM: Homo sapiens

<400> SEQUENCE: 8
gtactgagtg tatgtacagt tgaagtc                                27

<210> SEQ ID NO 9
<211> LENGTH: 27
<212> TYPE: DNA
<213> ORGANISM: Homo sapiens

<400> SEQUENCE: 9
ctttcaggaa caaatacagt tgaagtc                                27

<210> SEQ ID NO 10
<211> LENGTH: 28
<212> TYPE: DNA
<213> ORGANISM: Homo sapiens

<400> SEQUENCE: 10
tcaacttcag aaatgtacag ttgaagtc                                28

<210> SEQ ID NO 11
<211> LENGTH: 28
<212> TYPE: DNA
<213> ORGANISM: Homo sapiens

<400> SEQUENCE: 11
ggacacatac atacatacag ttgaagtc                                28

<210> SEQ ID NO 12
<211> LENGTH: 27
<212> TYPE: DNA
<213> ORGANISM: Homo sapiens

<400> SEQUENCE: 12
gtactgagtg tatgtacagt tgaagtc                                 27

<210> SEQ ID NO 13
<211> LENGTH: 26
<212> TYPE: DNA
<213> ORGANISM: Homo sapiens

<400> SEQUENCE: 13
tttcaggaac aaatacagtt gaagtc                                  26

<210> SEQ ID NO 14
<211> LENGTH: 27
<212> TYPE: DNA
<213> ORGANISM: Homo sapiens

<400> SEQUENCE: 14
actctcctat gatatacagt tgaagtc                                 27

<210> SEQ ID NO 15
<211> LENGTH: 27
<212> TYPE: DNA
<213> ORGANISM: Homo sapiens

<400> SEQUENCE: 15
actctcctat gatatacagt tgaagtc                                 27

<210> SEQ ID NO 16
<211> LENGTH: 27
<212> TYPE: DNA
<213> ORGANISM: Homo sapiens

<400> SEQUENCE: 16
aataatgcta gttatacagt tgaagtc                                 27

<210> SEQ ID NO 17
<211> LENGTH: 27
<212> TYPE: DNA
<213> ORGANISM: Homo sapiens

<400> SEQUENCE: 17
atggcgagtt aacatacagt tgaagtc					27

<210> SEQ ID NO 18
<211> LENGTH: 27
<212> TYPE: DNA
<213> ORGANISM: Homo sapiens

<400> SEQUENCE: 18
tattccatgg catatacagt tgaagtc					27

<210> SEQ ID NO 19
<211> LENGTH: 27
<212> TYPE: DNA
<213> ORGANISM: Homo sapiens

<400> SEQUENCE: 19
tatagctaac aatatacagt tgaagtc					27

<210> SEQ ID NO 20
<211> LENGTH: 26
<212> TYPE: DNA
<213> ORGANISM: Homo sapiens

<400> SEQUENCE: 20
gcaagtcctg tcatacagtt gaagtc					26

<210> SEQ ID NO 21
<211> LENGTH: 27
<212> TYPE: DNA
<213> ORGANISM: Homo sapiens

<400> SEQUENCE: 21
ttaaatggaa taattacagt tgaagtc					27

<210> SEQ ID NO 22
<211> LENGTH: 27
<212> TYPE: DNA
<213> ORGANISM: Homo sapiens

<400> SEQUENCE: 22
gacacataca tacatacagt tgaagtc					27

<210> SEQ ID NO 23
<211> LENGTH: 27
<212> TYPE: DNA
<213> ORGANISM: Homo sapiens

<400> SEQUENCE: 23
aaagcaatag cacatacagt tgaagtc					27

<210> SEQ ID NO 24
<211> LENGTH: 27
<212> TYPE: DNA
<213> ORGANISM: Homo sapiens

<400> SEQUENCE: 24
ttgtataaat catatacagt tgaagtc					27

<210> SEQ ID NO 25
<211> LENGTH: 27
<212> TYPE: DNA
<213> ORGANISM: Homo sapiens

<400> SEQUENCE: 25
tatagctaac aatatacagt tgaagtc                                27

<210> SEQ ID NO 26
<211> LENGTH: 27
<212> TYPE: DNA
<213> ORGANISM: Homo sapiens

<400> SEQUENCE: 26
cctaatcatc tacttacagt tgaagtc                                27

<210> SEQ ID NO 27
<211> LENGTH: 27
<212> TYPE: DNA
<213> ORGANISM: Homo sapiens

<400> SEQUENCE: 27
ttgtataaat catatacagt tgaagtc                                27

<210> SEQ ID NO 28
<211> LENGTH: 27
<212> TYPE: DNA
<213> ORGANISM: Homo sapiens

<400> SEQUENCE: 28
catgtcacat gaagtacagt tgaagtc                                27

<210> SEQ ID NO 29
<211> LENGTH: 27
<212> TYPE: DNA
<213> ORGANISM: Homo sapiens

<400> SEQUENCE: 29
agtgaggttt aacatacagt tgaagtc                                27

<210> SEQ ID NO 30
<211> LENGTH: 27
<212> TYPE: DNA
<213> ORGANISM: Homo sapiens

<400> SEQUENCE: 30
ctattttgga aacatacagt tgaagtc                                27

<210> SEQ ID NO 31
<211> LENGTH: 54
<212> TYPE: DNA
<213> ORGANISM: Homo sapiens

<400> SEQUENCE: 31
catgtcacat gaagtacagt tgaagtcgac ttcaactgta cattaggtaa ccac    54

<210> SEQ ID NO 32
<211> LENGTH: 55
<212> TYPE: DNA
<213> ORGANISM: Homo sapiens

<400> SEQUENCE: 32
attgtataaa tcatatacag ttgaagtcga cttcaactgt atctacatat tcata   55

<210> SEQ ID NO 33
<211> LENGTH: 54
<212> TYPE: DNA
<213> ORGANISM: Homo sapiens

```
<400> SEQUENCE: 33
tcttttgttg catatacagt tgaagtcgac ttcaactgta tgtatgcatt tctg      54

<210> SEQ ID NO 34
<211> LENGTH: 54
<212> TYPE: DNA
<213> ORGANISM: Homo sapiens

<400> SEQUENCE: 34
ccctctccta cacatacagt tgaagtcgac ttcaactgta cattatacta ctaa      54
```

MUTATED SLEEPING BEAUTY TRANSPOSASE

The present invention relates to improved transposase polypeptides having increased solubility. The enzyme of the invention was developed based on the Sleeping Beauty (SB) transposase. The invention provides further nucleic acids, vectors and recombinant cells encoding or containing the improved transposase, as well as a transposase system. Furthermore provided are medical and non-medical uses of the transposase of the invention for gene delivery. The invention is in particular useful as a tool for gene delivery in genetically modified cell based therapeutic approaches for treating various diseases.

BACKGROUND OF THE INVENTION

DNA transposons are discrete genetic entities ubiquitously spread across the tree of life that can move within and between genomes. They are prominent evolutionary forces fostering genome remodeling, evolutionary changes, transmission of antibiotic resistance determinants, and the development of new biological functions such as adaptive immunity. Due to their natural properties, DNA transposons have been successfully utilized as artificial gene carriers and insertional mutagens in transgenesis and functional genomics.

The use of DNA transposons for genome manipulations in vertebrates was first enabled by the reconstruction of the Sleeping Beauty (SB) transposon from the genomes of salmonid fish. The applied SB transposon system consists of a transposon, made up of a gene of interest (genetic cargo) flanked by the specific SB inverted repeats (IRs), and the transposase protein expressed from a separate plasmid or locus. The transposase specifically binds to the IRs, cuts the transposon from a donor locus and integrates it in a new genomic location. SB has exceptionally high insertion efficiency in vertebrate genomes, which has allowed its development into a prime genetic tool, successfully applied in transgenesis of higher organisms, stem cell generation and cancer gene discovery.

Importantly, SB is now also applied as non-viral gene delivery vector in a number of clinical trials five of which aim to ex vivo modify T cells by incorporating a chimeric antigen receptor (CAR) against malignancy-specific antigens. In these studies, the SB transposase inserts a CAR gene-carrying transposon from a donor plasmid into the genome of patient-derived T cells, which are successively re-infused in the cancer patient. The introduced CARs provide the T cells with new specificities to distinctively target the cancer cells and trigger effector functions upon antigen encounter. Most successful CAR-T therapies target the CD19 antigen that is overexpressed in malignant B cells. This therapy has shown unprecedented response rates (70%-90%) in the treatment of acute and chronic leukemia and will likely enter mainstream care for many B cell malignancies in the next years. However, for the treatment of large number of patients, there is a pressing need to improve manufacturing feasibility and safety, which are also critical requirements of gene therapy in general.

Because SB is a simple binary synthetic system, it is cheaper, easier and faster to produce and implement than viral vectors. This provides a particular advantage especially for single-use and personalized applications. Use of the non-viral SB vector also reduces the risks of undesired immune response activation in patients, which constitutes a major safety concern connected to the use of viral vectors in gene therapy applications in general and in cancer immunotherapy (i.e. CAR-T cell therapy) in particular. Moreover, in contrast to gamma-retroviral and lentiviral vectors that preferentially insert into actively transcribed or regulatory regions, SB presents a close-to-random genomic integration pattern reducing the risk of insertional mutagenesis and genotoxicity. Differently to genome editing nucleases as zinc-finger, TALENs, and Cas9, the SB transposase directly and precisely integrates its cargo into the chromosome without generating potentially harmful double-strand breaks at the target locus. Therefore, SB's insertion rates and safety do not depend on the efficiency of the repair machinery in the target cells. These advantages make SB the only non-viral gene delivery vehicle used for CAR-T cell engineering in clinical trials, which has triggered considerable commercial interest in the SB system in the last few years.

Although the SB system typically has lower gene-transfer efficiency than viral vectors, novel strategies—such as improved design and delivery methods for its components, as well as selective propagation of CAR positive cells—have recently increased the success of SB-mediated T cell engineering to levels similar to viral approaches. Despite these improvements, important issues remain. In particular, long-term transposase expression can result in uncontrolled ongoing transposition, potentially leading to transgene remobilization, undesired insertion events, genome instability and cytotoxicity. Moreover, insertion of the SB transposase gene from the expression vector (e.g. by homologous recombination) may result in infinite transposase production and unintended acquisition of the transposase promoter might cause activation of oncogenes or disrupt gene regulatory networks in the target cells. This poses concerns regarding the safety of the current SB system and highlights the need for technological advances to reduce or alleviate these risks.

To circumvent these risks, direct delivery of the SB transposase protein is highly desired, as it can help to achieve tighter efficiency/temporal control and improve the safety of transposition-based cell engineering, especially for therapeutic applications. Nevertheless, the production of active recombinant SB transposase in sufficient quantity and quality has been challenging to date.

The above problem is solved in a first aspect by a transposase polypeptide comprising at least one mutated amino acid residue compared to a reference amino acid sequence—such as a non-mutated but artificial transposase or a wild-type enzyme—of the transposase, wherein the at least one mutated amino acid residue is located within the catalytic domain of the transposase. The catalytic domain is preferably within an amino acid sequence between residues 150 and 250 of for example SB100x (SEQ ID NO: 2). Reference transposases according to the invention are preferably SB transposases either as wild-type enzymes or genetically engineered enzymes such as SB10, SB11 or SB100X.

The transposase polypeptide has several surprising advantages compared to the prior art SB100x enzyme. The invention shows in the example section that the transposase of the invention has a higher protein yield in recombinant protein expression, increased solubility, which is advantageous for delivery of the protein via electroporation (better soluble in the electroporation buffer), the enzyme is more stable and less prone to protein degradation and in particular more thermostable than the prior art enzyme which also is advantageous during electroporation.

The present invention provides a safe and effective strategy to achieve efficient, stable and controlled genetic engineering of mammalian cells via the direct delivery of a mutated transposase variant. The new transposase variant of the invention is suitable for large-scale recombinant protein production and transfection, which allows for successful engineering of a range of mammalian cell lines and the manufacture of Chimeric Antigen Receptor (CAR) T-cells. The present strategy, that was named "SBprotAct", provides a novel approach to alleviate safety issues and enables maximal control of the transposase system in clinical applications. Finally, the transposase of the invention proved to create less insertions per cell at the same transgenesis rate and hence allows for a tightly controlled gene delivery.

The term "transposase" as used herein refers to an enzyme that is a component of a functional nucleic acid-protein complex capable of transposition and which is mediating transposition. The term "transposase" also refers to integrases from retrotransposons or of retroviral origin. A "transposition reaction" as used herein refers to a reaction where a transposon inserts into a target nucleic acid. Primary components in a transposition reaction are a transposon and a transposase or an integrase enzyme. For example, the transposase system according to the invention is preferably a so called "Sleeping Beauty (SB)" transposase. In certain aspects, the transposase is an engineered enzyme with improved characteristics such as increased enzymatic function. Some specific examples of an engineered SB transposases include, without limitation, SB10, SB11 or SB100x SB transposase (see, e.g., Mates et al., Nat. Gen. 2009, incorporated herein by reference). Other transposition systems can be used, e.g., Ty1 (Devine and Boeke, 1994, and WO 95/23875), Tn7 (Craig, 1996), Tn 10 and IS 10 (Kleckner et al. 1996), Mariner transposase (Lampe et al., 1996), Tc1 (Vos et al., 1996), Tn5 (Park et al., 1992), P element (Kaufman and Rio, 1992) and Tn3 (Ichikawa and Ohtsubo, 1990), bacterial insertion sequences (Ohtsubo and Sekine, 1996), retroviruses (Varmus and Brown 1989), and retrotransposon of yeast (Boeke, 1989).

In preferred embodiments of the present invention the transposase is a Sleeping Beauty (SB) transposase, and preferably is SB100X (SEQ ID NO: 2) or an enzyme derived from SB100X.

Hence, the transposase polypeptide according to the invention is a polypeptide having transposase activity, wherein the at least one mutated amino acid residue is a residue that is located between amino acid 150 and 250 of SB transposase, preferably SB100X transposase.

In some embodiments it is preferably that the at least one mutated amino acid residue is at least two mutated amino acid residues, or at least three, four, five or more amino acids. It is preferably that the transposase polypeptide of the invention when its sequence is aligned with the sequence of an SB transposase, preferably SB100X, is mutated in any one of amino acids 170 to 180 and/or 207 to 217. More preferably the at least one mutated amino acid residue is selected from amino acid 176 and/or 212 of SB transposase, preferably of SB100X.

Most preferably the at least one mutated amino acid residue is mutated into a serine residue, and preferably is C176S, or C176S and I212S.

In other embodiments, the transposase polypeptide of the invention further comprises an amino acid sequence having at least 60%, 70%, 80%, 90%, 95%, 96%, 97%, 98%, 99%, most preferably 100% sequence identity to the amino acid sequence between residues 150 to 250 as shown in SEQ ID NO: 1 (hsSB). It is preferred that the transposase polypeptide includes at least a C176 mutation, preferably C176S, compared to the sequence in SEQ ID NO: 2. Even more preferably the transposase polypeptide further includes the mutation at position 1212, preferably I212S.

In some embodiments the transposase polypeptide of the invention comprises an amino acid sequence having at least 60%, 70%, 80%, 90%, 95%, 96%, 97%, 98%, 99%, most preferably 100% sequence identity to the full length amino acid sequence as shown in SEQ ID NO: 1 or 3 (hsSB). Preferably, although the degree of sequence identity is in some embodiments below 100%, the above indicated at least one mutation shall be present in the transposase polypeptide of the invention.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region—preferably over their full length sequences—, when compared and aligned for maximum correspondence over the comparison window or designated region) as measured using a sequence comparison algorithms, or by manual alignment and visual inspection (see, e.g., NCBI web site). In a particular embodiment, for example when comparing the protein or nucleic acid sequence of the transposase of the invention to for example a reference (non-mutated transposase), the percentage identity can be determined by the Blast searches provided in NCBI; in particular for amino acid identity, those using BLASTP 2.2.28+ with the following parameters: Matrix:BLOSUM62; Gap Penalties:Existence: 11, Extension: 1; Neighboring words threshold: 11; Window for multiple hits: 40.

In addition, in some embodiments, the transposase polypeptide of the invention has an increased solubility compared to a reference non-mutated transposase polypeptide, preferably wherein the reference non-mutated transposase polypeptide is SB100X transposase, preferably as shown in SEQ ID NO: 2 (non-mutated SB100X).

In another aspect of the invention there is provided a polynucleotide comprising a nucleic acid sequence encoding for a transposase polypeptide as described herein above, preferably wherein the polynucleotide is RNA or DNA. For example RNA may be provided in the form of messenger RNA (mRNA) that allows for a direct translation into the transposase polypeptide of the invention if the mRNA is introduced into a biological cell.

Another aspect of the invention pertains to a vector comprising a polynucleotide of the invention. Also provided is an expression construct, comprising an expressible polynucleotide encoding a transposase polypeptide of the invention and a promoter element, wherein the promoter element is operably linked to the expressible polynucleotide to allow for the expression of the polynucleotide.

Also provided is a recombinant cell, comprising a transposase polypeptide of the invention, a polynucleotide of the invention, or a vector and/or an expression construct of the invention.

The recombinant cell is preferably a cell suitable for recombinant protein expression, preferably for recombinant protein expression of the transposase polypeptide of the invention. Such as a bacterial cell or eukaryotic cell, most preferably a bacterial cell such as *E. coli* or an insect cell, such as *Drosophila* S2 cell or a mammalian cell such as HEK293T cell.

Yet another aspect relates to a transposon system comprising
(a) a transposon unit containing inverted terminal repeats (ITRs) or direct terminal repeats (DTRs) that flank a sequence of interest to be inserted into the genome of a target cell; and
(b) a transposase polypeptide, a polynucleotide, a vector and/or an expression construct as described herein above.

Herein, the term "transposon unit" shall refer to the nucleic acid construct that constitutes the transposon genetic sequence with the target sequence that is to be introduced into a target cell genome. Usually a transposon unit will be nucleic acid and may be a vector of any form suitable for transposition.

As used herein, the term "inverted terminal repeat" refers to a sequence located at one end of a transposon unit that can be cleaved by a transposase polypeptide when used in combination with a complementary sequence that is located at the opposing end of the vector or transposon unit. The pair of inverted terminal repeats is involved in the transposition activity of the transposon of the transposon unit of the present disclosure, in particular involved in DNA addition or removal and excision and integration of DNA of interest. In one example, at least one pair of an inverted terminal repeat appears to be the minimum sequence required for transposition activity in a plasmid. In another example, the transposon unit of the present disclosure may comprise at least two, three or four pairs of inverted terminal repeats. As would be understood by the person skilled in the art, to facilitate ease of cloning, the necessary terminal sequence may be as short as possible and thus contain as little inverted repeats as possible. Thus, in one example, the transposon unit of the present disclosure may comprise not more than one, not more than two, not more than three or not more than four pairs of inverted terminal repeats. In one example, the transposon unit of the present disclosure may comprise only one inverted terminal repeat. Whilst not wishing to be bound by theory, it is envisaged that having more than one inverted terminal repeat may be disadvantageous as it may lead to non-specific transposase binding to the multiple inverted terminal repeats and resulting in the removal of desired sequence or insertion of undesirable sequences. The inverted terminal repeat of the present disclosure may form either a perfect inverted terminal repeat (or interchangeably referred to as "perfect inverted repeat") or imperfect inverted terminal repeat (or interchangeably referred to as "imperfect inverted repeat"). As used herein, the term "perfect inverted repeat" refers to two identical DNA sequences placed at opposite direction. The above descriptions for transposon units with ITR also apply for transposon units with DTRs.

A transposon system that could be used with the inventive transposon polypeptide/nucleic acid of the invention is for example disclosed in WO 2017/050448 A1, which is included in the present disclosure by reference.

A transposon system according to the invention is preferable, wherein said transposon unit of (a) is in the form of a minicircle. However, the transposon unit may be other nucleic acid systems. However, minicircles are preferable in the context of T cell engineering.

The transposon system of the invention in preferred embodiments is an SB transposon system.

Another aspect of the invention then pertains to the use of a transposon system as described for gene delivery into a target cell. The gene delivery is preferably an ex vivo gene delivery into a target cell, such as a target cell selected from a stem cell, such as a hematopoietic or embryonic stem cell, T-cell, B-Cell or Chinese Hamster Ovary (CHO) cell. Most preferably is the system or the compounds of the invention used in the generation of CAR T-cells.

The term "chimeric antigen receptor" (CAR), as used herein, refers to an extracellular antigen-binding domain that is fused to an intracellular signaling domain of a cell, such as a T cell or a NK-92 cell.

Further provided is a method for gene delivery into a target cell comprising the following steps:
(a) bringing into contact the transposon system as described with a target cell;
(b) culturing said target cell under conditions permissive to the culture of said target cell.

In another aspect, a pharmaceutical composition is provided, comprising a transposase polypeptide, a polynucleotide, a vector, and/or an expression construct, together with a pharmaceutically acceptable carrier and/or excipient.

Another aspect then pertains to a kit comprising
(a) a transposon unit containing inverted terminal repeats (ITRs) or DTRs that flank a sequence of interest to be inserted into the genome of a target cell; and
(b) a transposase polypeptide, a polynucleotide, a vector, and/or an expression construct of the invention as described herein.

The compounds and systems of the invention may preferably find application in medicine. Therefore, such compounds and systems of the invention are preferably for use in the treatment of a disease. Such diseases may be proliferative disease, such as cancer. For a cancer treatment, the invention may be used in context of the generation of modified immune cells. For example, the invention can be used to introduce into immune cells T cell receptors (TCR) or CARs or other immune molecules, to strengthen and target a patient's immune system against cancer cells. Immune cells that can be modified may be selected from human T lymphocytes or B cells. Other diseases that could benefit from the invention are genetic disorders that are characterized by the loss of a gene function. In such diseases cells could be modified with the invention to include a healthy copy of the disease associated gene. Other target cells that are preferably used in context with the invention are stem cells such as, for example, embryonic, or adult stem cells, such as hematopoietic stem cells.

The following figures, sequences, and examples merely serve to illustrate the invention and should not be construed to restrict the scope of the invention to the particular embodiments of the invention described in the examples. All references as cited herein are hereby incorporated in their entirety by reference.

FIG. 1: Rational mutagenesis of the SB100X transposase

Figure 2:
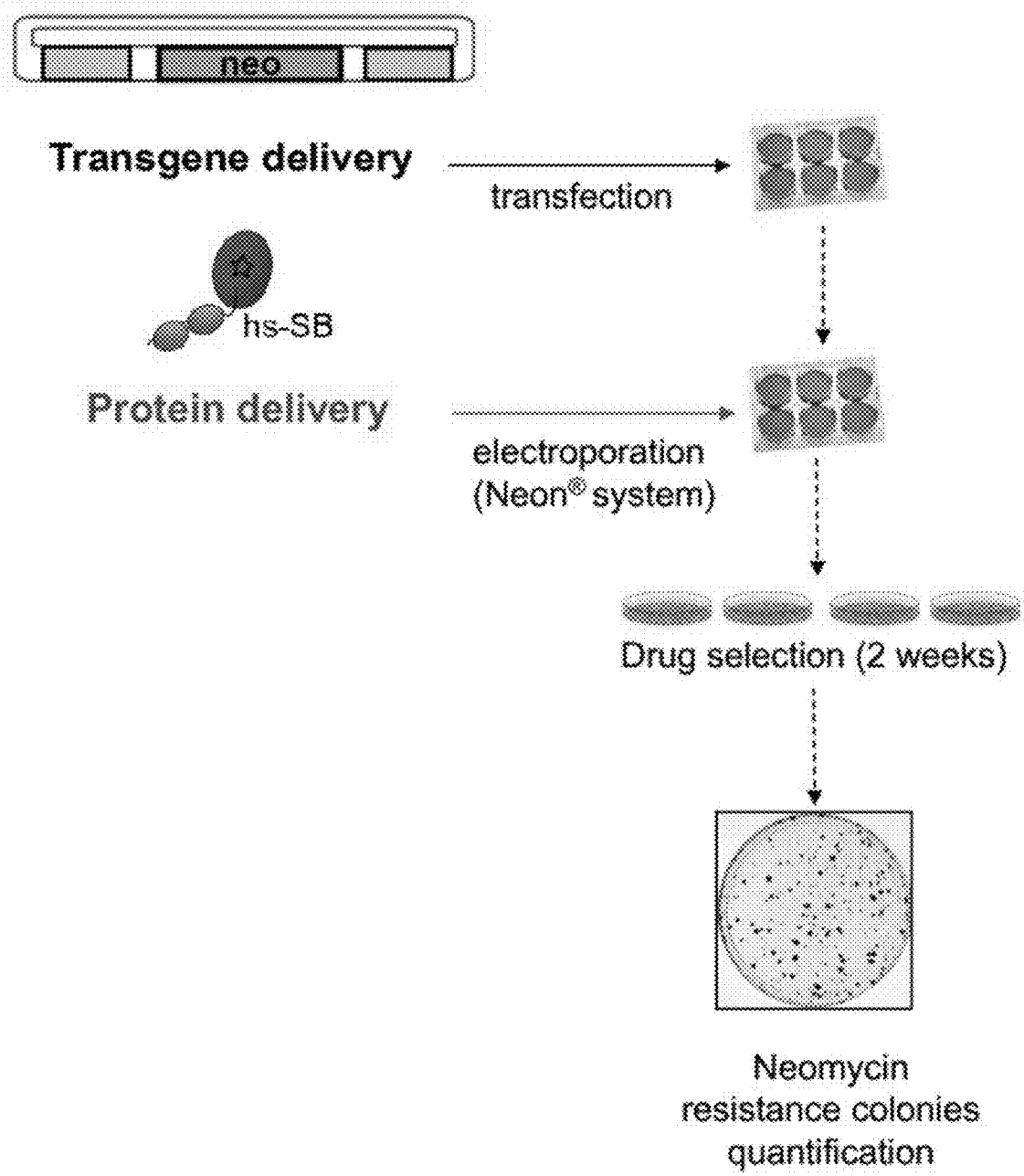

FIG. 2: Schematic representation of the SBprotAct engineering procedure.

Figure 3:
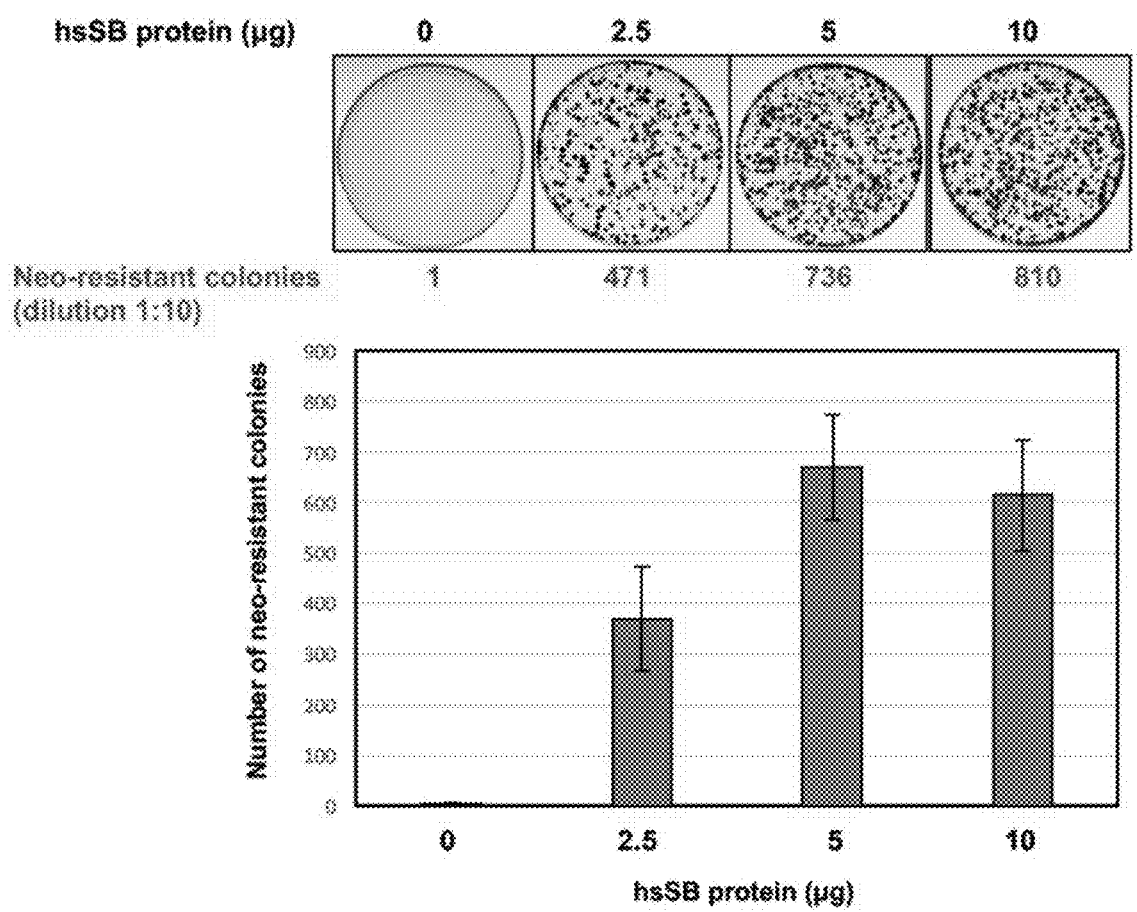

FIG. 3: Transgene (neomycin) insertions are driven by transposition activity of the transfected hsSB transposase.

FIG. 4: Insertion sites as derived by sequence analysis of the neomycin locus from 11 isolated neomycin positive HeLa cell clones. Insertions of SB IRs correctly occur at TA dinucleotides.

Figure 5:
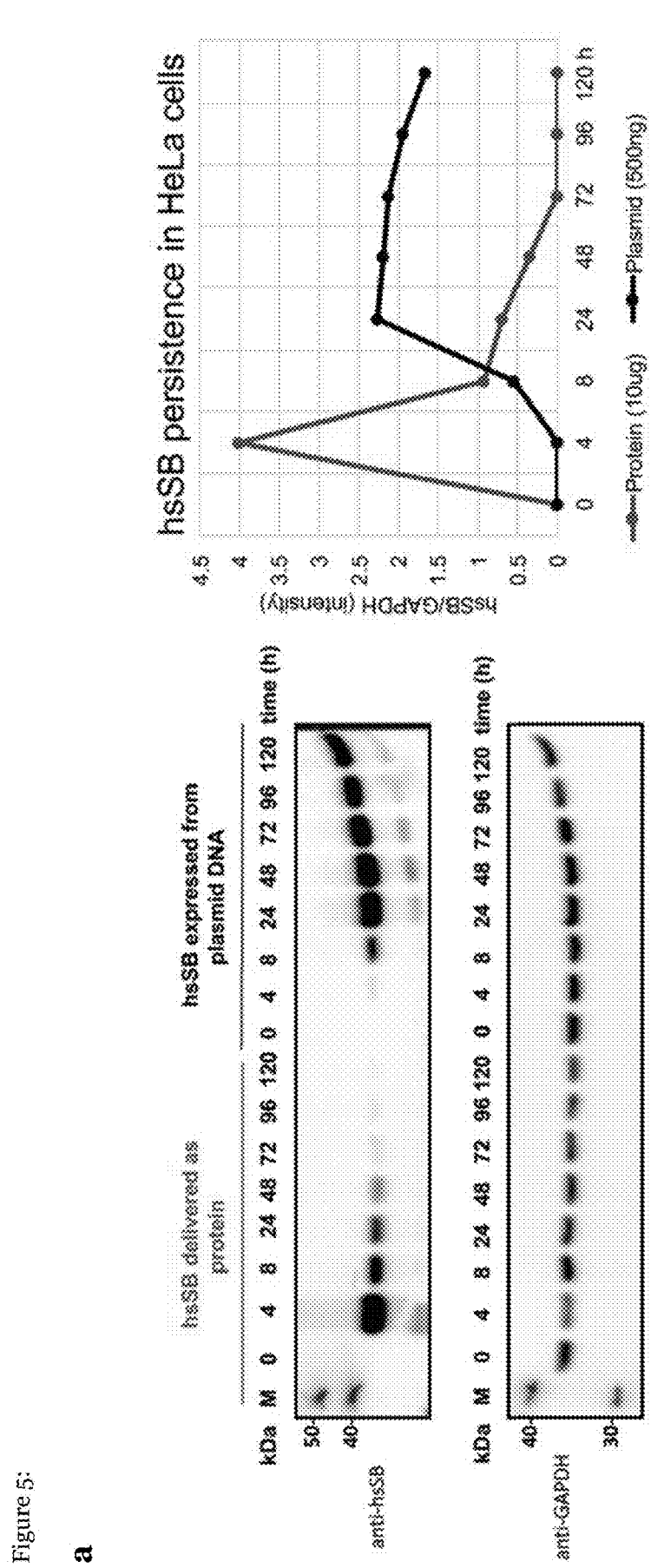
Figure 5:
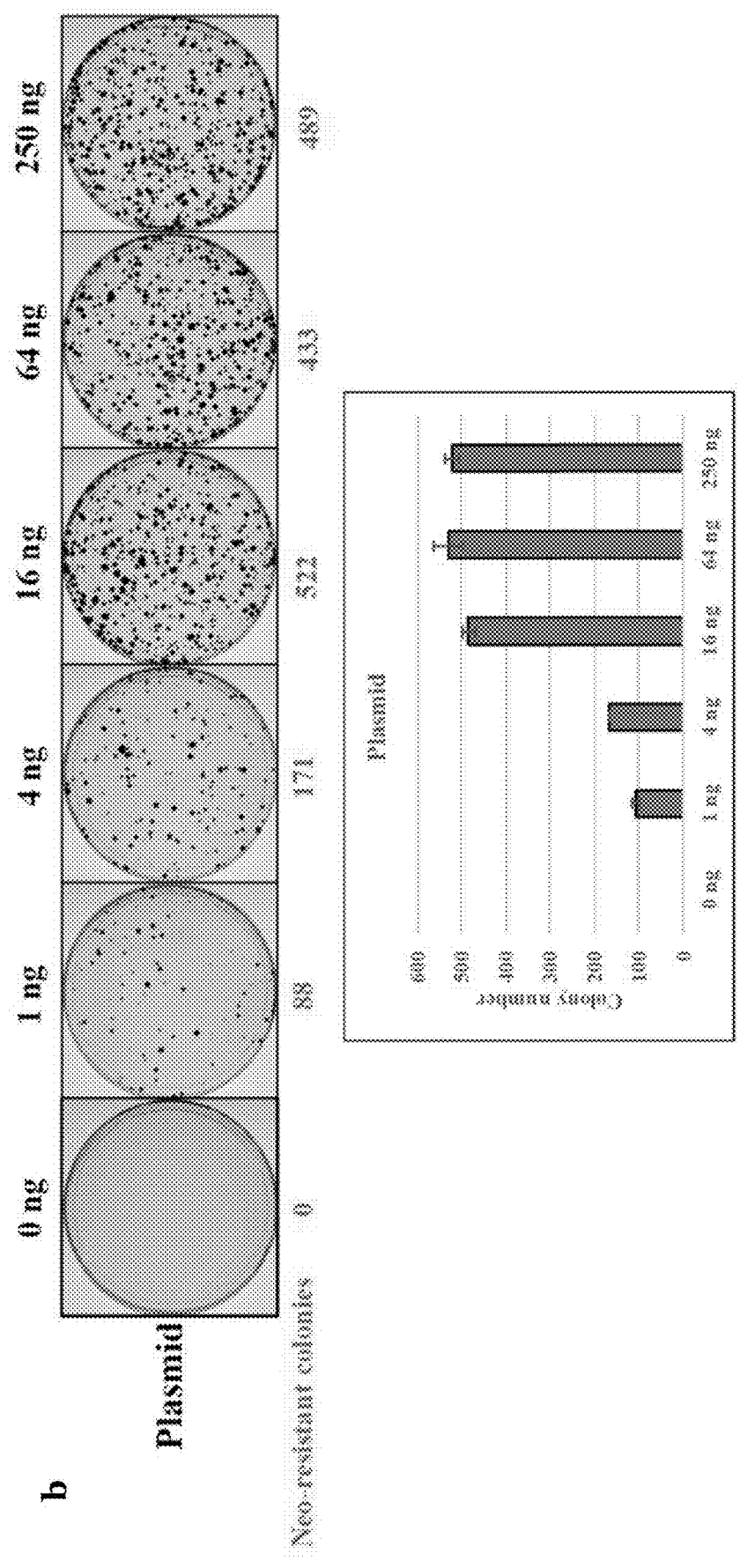
Figure 5:
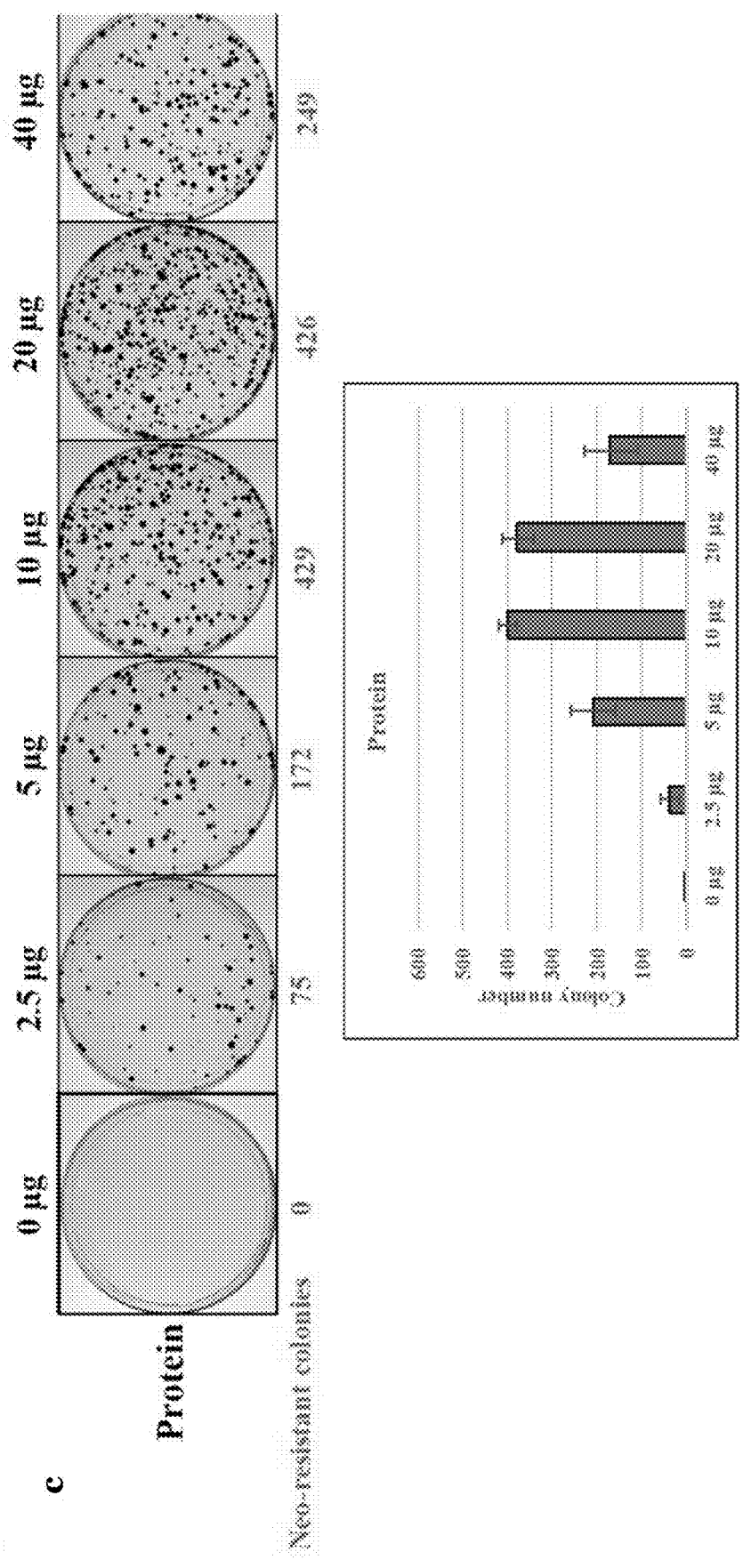
Figure 5:
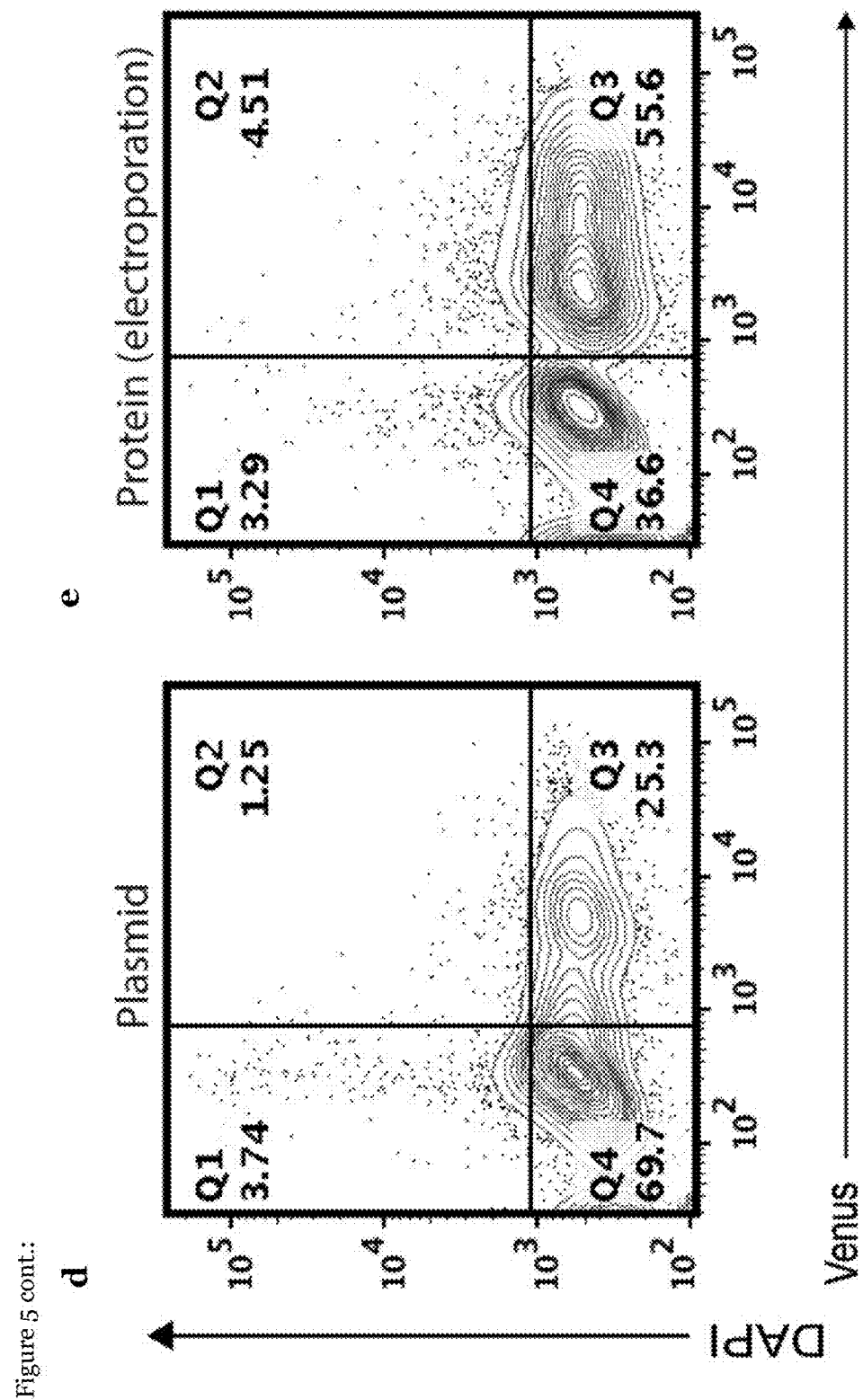

FIG. 5: Delivery of hsSB by protein or plasmid. (a): retention of hsSB delivered into HeLa cells as protein or expressed from plasmid DNA; (b) and (c): Representative transposition assays in HeLa cells demonstrate comparable transgene (neomycin resistance) insertion rate when using the hsSB transposase delivered as a plasmid (b) or as a protein (c). Error bars indicate the standard error of the mean from 2 independent experiments (n=2); (d) and (e): representative flow cytometric analysis by Fluorescence Activated Cell Sorting (FACS) of HeLa cells transfected with Venus-carrying transposon plasmid and: (a) hsSB plasmid, or (b) hsSB delivery by electroporation. Cells that acquired the transposon plasmid were sorted 2 days post-transfection; transposition efficiency was quantified 21 days later by FACS analysis.

Figure 6:
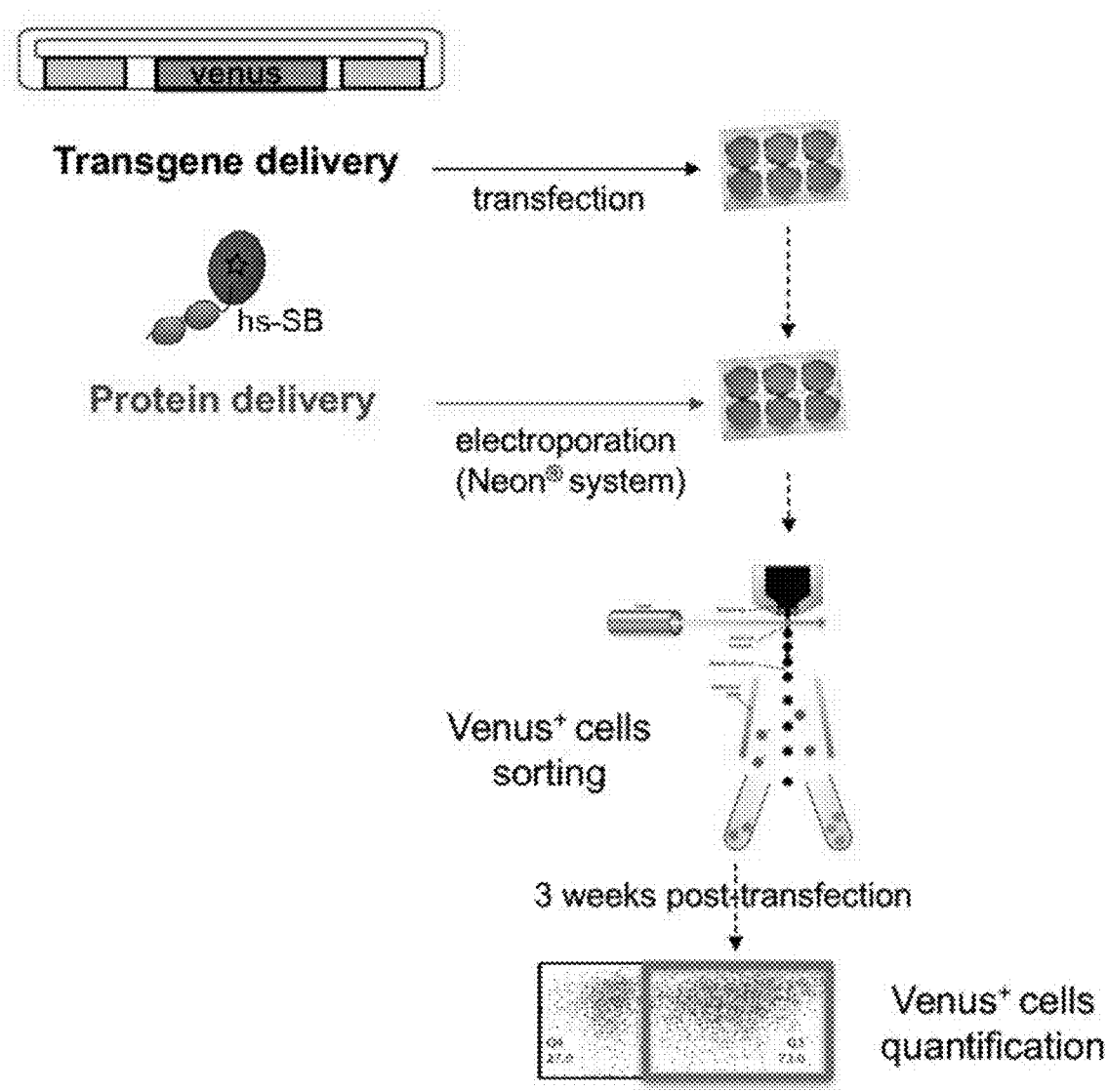

FIG. 6: Schematic representation of the SBprotAct engineering procedure with quantification by cell sorting.

Figure 7:
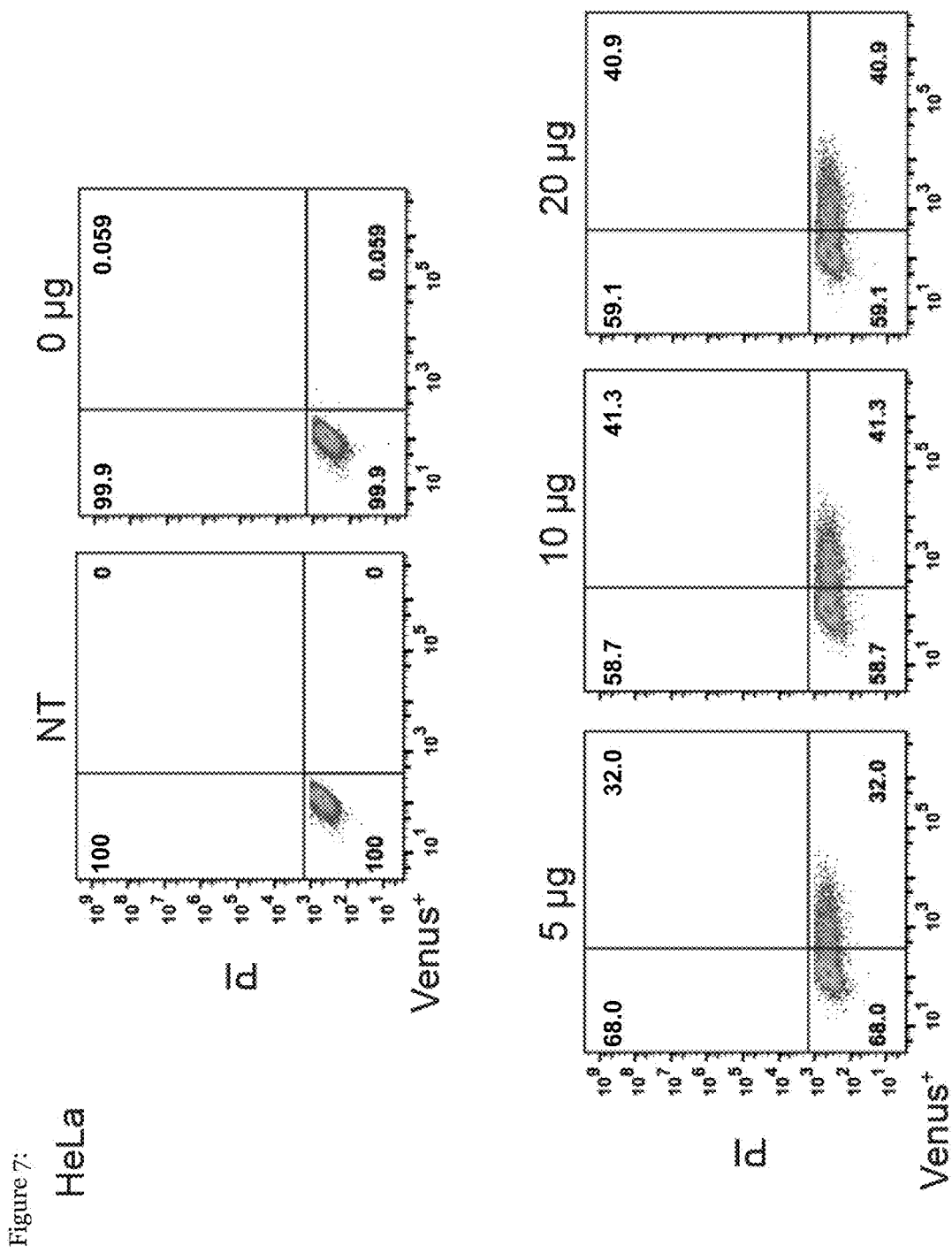

FIG. 7: Representative flow cytometric analysis of HeLa cells transfected with Venus-carrying transposon plasmid and electroporated with hsSB transposase.

Figure 8:
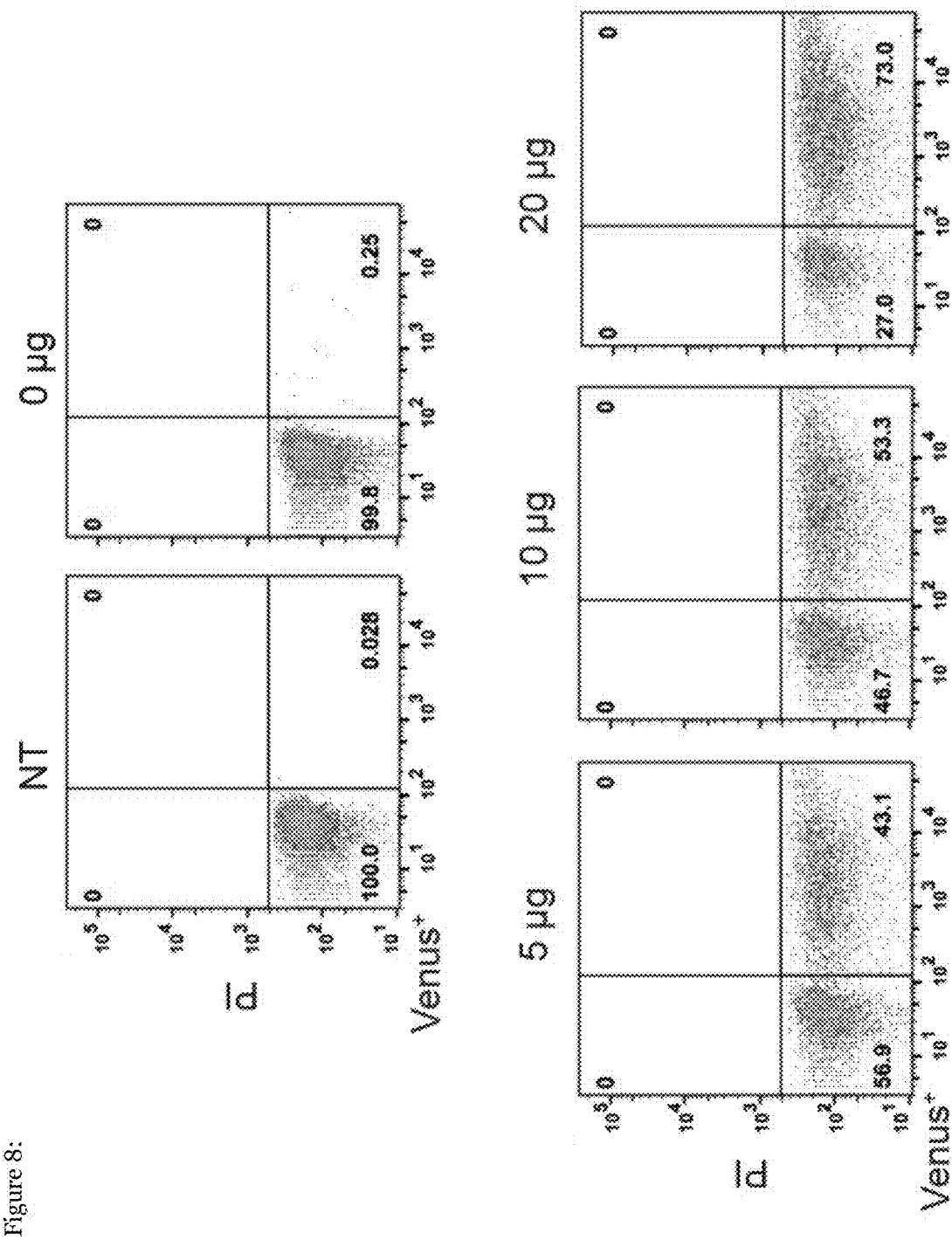

FIG. 8: Representative flow cytometric analysis of Chinese Hamster Ovary (CHO) cells transfected with Venus-carrying transposon plasmid and electroporated with hsSB transposase.

Figure 9A:
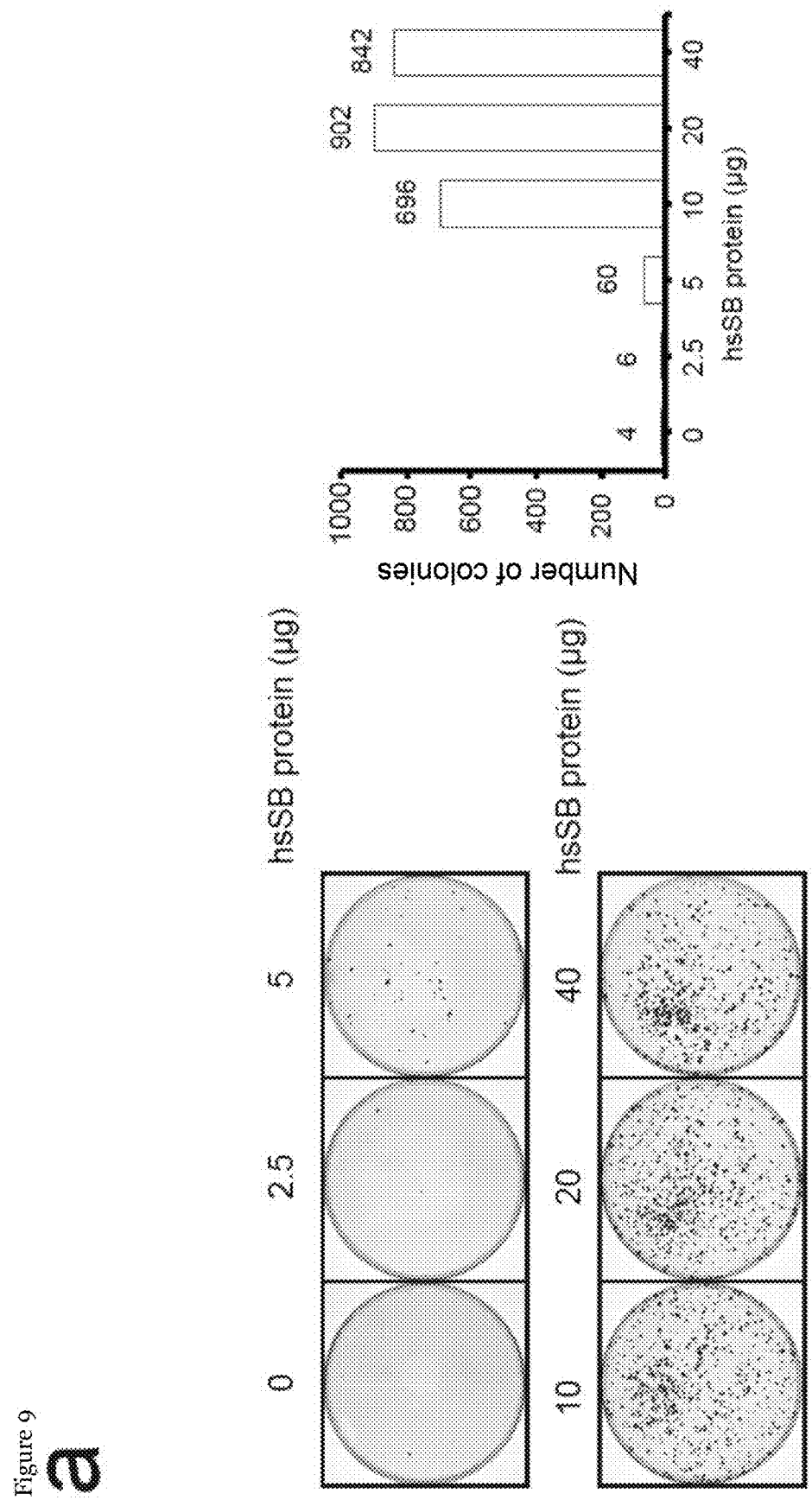
Figure 9:
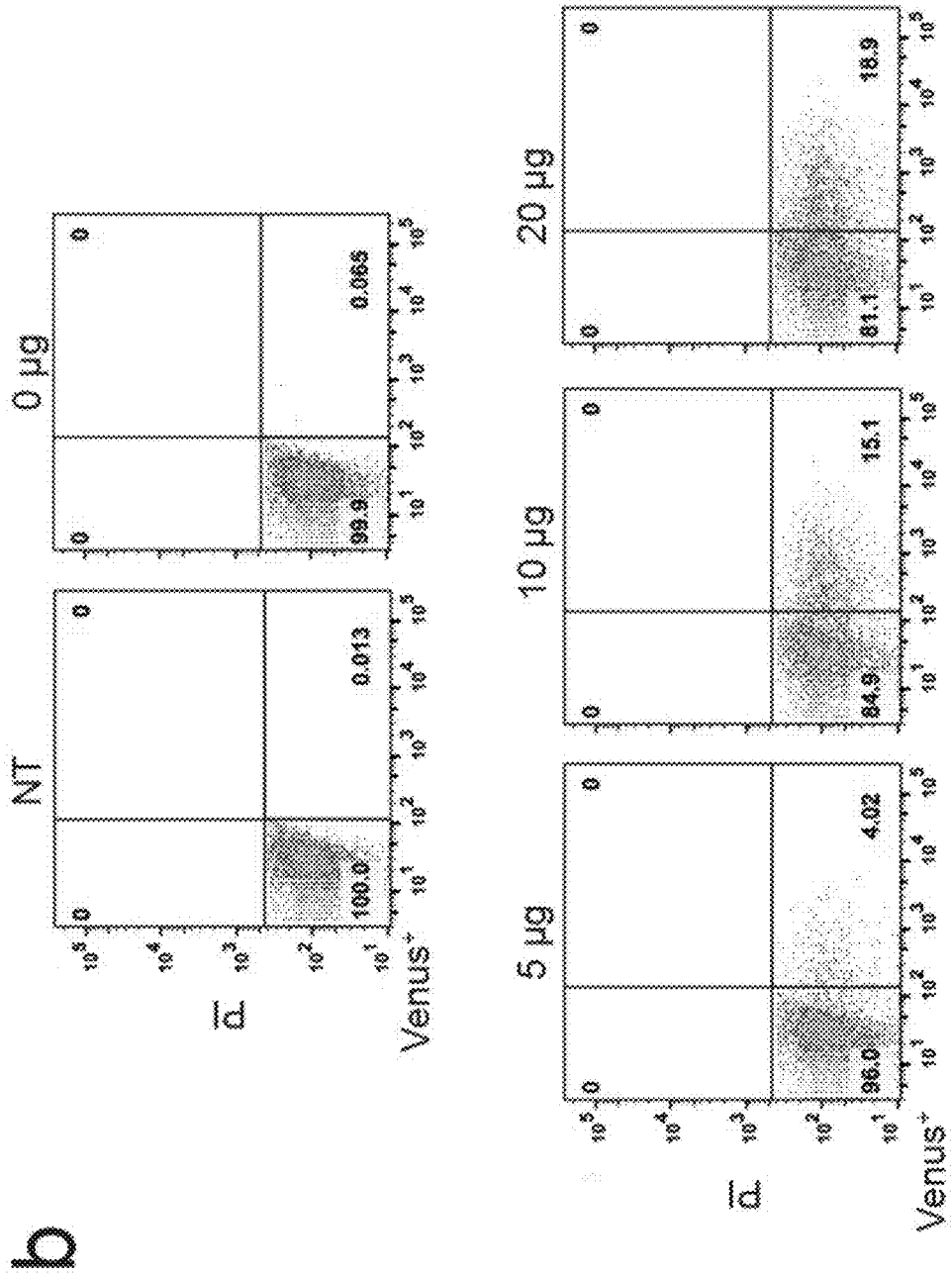
Figure 9:
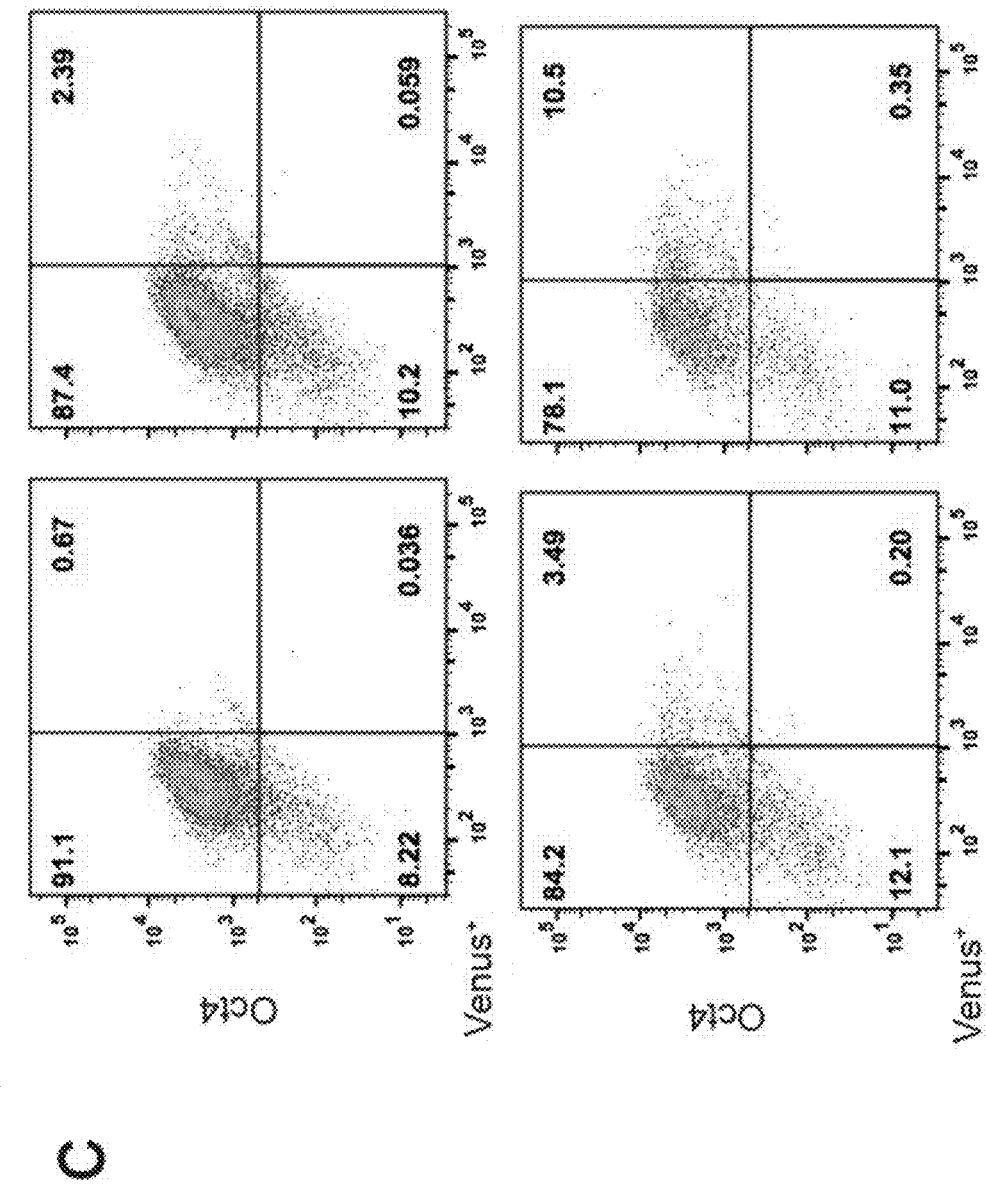

FIG. 9: Genetic engineering of mESCs by direct delivery of the hsSB transposase protein.

FIG. 10: Transgenesis efficiency of the SBprotAct system in different cell lines as quantified by flow cytometric analysis. Errors are indicated as standard deviation (n=2).

(hsSB)
SEQ ID NO: 1
MGKSKEISQDLRKRIVDLHKSGSSLGAISKRLAVPRSSVQTIVRKYKHHGT

TQPSYRSGRRRVLSPRDERTLVRKVQINPRITAKDLVKMLEETGTKVSIST

VKRVLYRHNLKGHSARKKPLLQNRHKKARLRFATAHGDKDRTFWRNVLWSD

ETKIELFGHNDHRYVWRKKGEASKPKNTIPTVKHGGGSIMLWGCFAAGGTG

ALHKIDGSMDAVQYVDILKQHLKTSVRKLKLGRKWVFQHDNDPKHTSKVVA

KWLKDNKVKVLEWPSQSPDLNPIENLWAELKKRVRARRPTNLTQLHQLCQE

EWAKIHPNYCGKLVEGYPKRLTQVKQFKGNATKY (non mutated SB100X)
SEQ ID NO: 2
MGKSKEISQDLRKRIVDLHKSGSSLGAISKRLAVPRSSVQTIVRKYKHHGT

TQPSYRSGRRRVLSPRDERTLVRKVQINPRITAKDLVKMLEETGTKVSIST

VKRVLYRHNLKGHSARKKPLLQNRHKKARLRFATAHGDKDRTFWRNVLWSD

ETKIELFGHNDHRYVWRKKGEA*C*KPKNTIPTVKHGGGSIMLWGCFAAGGTG

ALHKIDG*I*MDAVQYVDILKQHLKTSVRKLKLGRKWVFQHDNDPKHTSKVVA

KWLKDNKVKVLEWPSQSPDLNPIENLWAELKKRVRARRPTNLTQLHQLCQE

EWAKIHPNYCGKLVEGYPKRLTQVKQFKGNATKY (hsSB for recombinant expression)
SEQ ID NO: 3
*GPM*MGKSKEISQDLRKRIVDLHKSGSSLGAISKRLAVPRSSVQ-TIVRKYKH

HGTTQPSYRSGRRRVLSPRDERTLVRKVQINPRTTAKDLVKMLEETGTKVS

ISTVKRVLYRHNLKGHSARKKPLLQNRHKKARLRFATAHGDKDRTFWRNVL

WSDETKIELFGHNDHRYVWRKKGEASKPKNTIPTVKHGGGSIMLWGCFAAG

GTGALHKIDGSMDAVQYVDILKQHLKTSVRKLKLGRKWVFQHDNDPKHTSK

VVAKWLKDNKVKVLEWPSQSPDLNPIENLWAELKKRVRARRPTNLTQLHQL

CQEEWAKIHPNYCGKLVEGYPKRLTQVKQFKGNATKY
(underlined are mutated or to-be mutated residues. Bold and italic are residues introduced for recombinant protein expression)

EXAMPLES

Example 1: Rational Mutagenesis of the SB100X Transposase

In FIG. 1, (a) left side the crystal structure of the SB100X transposase (hereafter referred to as SB) catalytic domain is shown. Residues mutated to serines for the generation of the hsSB variant are shown as sticks in magenta. Right: Amino acid sequence of the full length hsSB transposase variant used for recombinant protein production. Bold underlined characters in magenta indicate serines substituting C176 and I212 respectively in the SB100X sequence. Residues colored in blue have been introduced at the N-terminus for recombinant protein production.

Figure 1G:
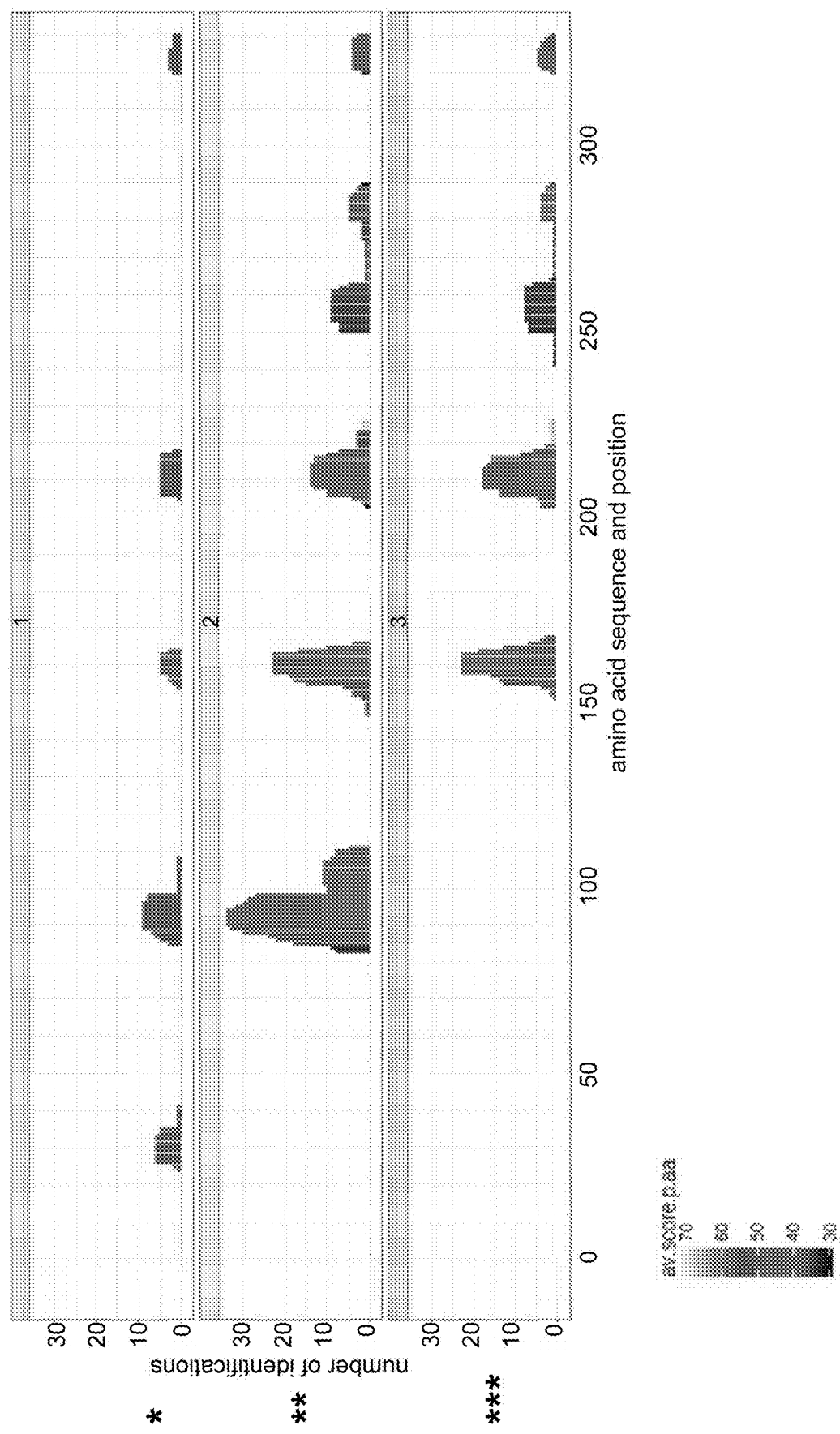
Figure 1:
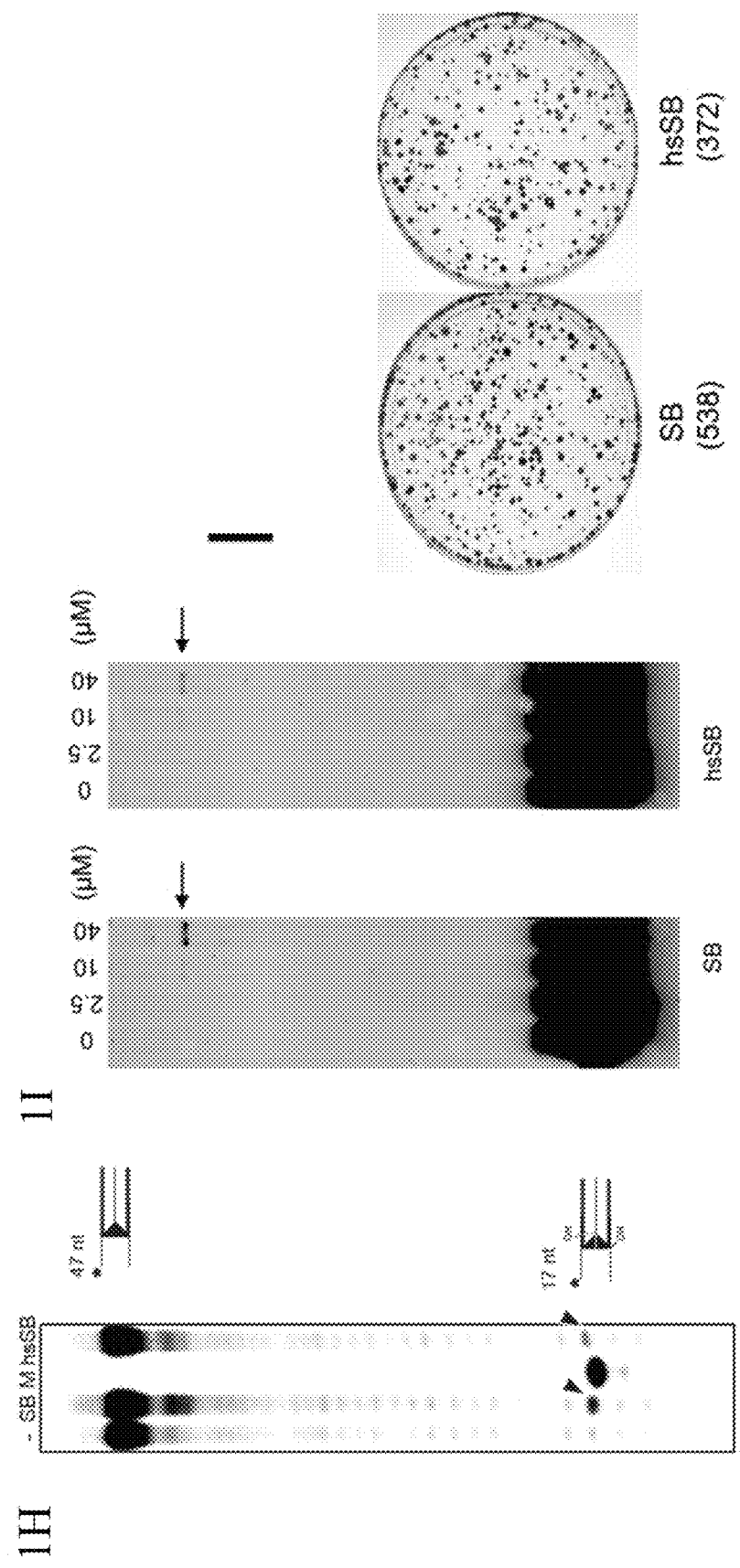

FIG. 1(b) shows the recombinant production of hsSB protein of the invention. SDS-PAGE analysis of purified hsSB protein variant is provided. hsSB is recombinantly produced in E. coli (fused to N-terminal purification and solubility tags) in high quantity. hsSB is highly pure after tag removal and size exclusion chromatography (SEC). Purification yields of hsSB are shown in FIG. 1c. Size exclusion chromatogram showing that hsSB is recombinantly produced at significantly higher yields (roughly double amounts) compared to SB, indicating improved solubility of the hsSB variant. High solubility of hsSB in electroporation buffer is shown in FIG. 1d. hsSB can be concentrated up to 50 fold (corresponding to 20 mg/ml), whereas SB undergoes precipitation at concentrations higher than 7 mg/ml. hsSB is highly soluble in the low salt R buffer (used for electroporation), even at high protein concentration. While some precipitation is observed upon concentration, the vast majority of hsSB stays in the soluble fraction. SDS-PAGE analysis of purified SB proteins upon incubation at 37° C. is shown in FIG. 1e. SB exhibits degradation (degradation products indicated by asterisks) even upon short incubation at physiological temperature, while hsSB does not. Also, as shown in FIG. 1f, hsSB is more thermostable than SB. CD measurements of both proteins in close to physiological (200 mM NaCl, pH 7.5) buffer condition. However, hsSB has the same fold as SB, as shown in the left panel. Nonetheless, hsSB is significantly more thermostable; it still does not completely unfold at 95° C. (right panel). Considering that electroporation heats the sample, this property is highly advantageous for protein transfection. Finally, upon long-term storage hsSB is better preserved than SB (FIG. 1g). Left panel: SDS-PAGE analysis of purified SB proteins upon long-term storage at −80° C., showing that SB undergoes significant degradation after freezing, while hsSB does not. Right panel. Mass spectrometry analysis of the bands indicated by blue boxes and asterisks on the left confirms that the bands correspond to degradation products of the SB protein.

Example 2: Gene Delivery Using hsSB Transposase into Hela Cells

A strategy for gene delivery is depicted in FIG. 2. Transgene (neomycin resistance gene) insertions are driven by transposition activity of the transfected hsSB transposase (FIG. 3). Top: Representative transposition assay in HeLa cells. Number of neomycin resistant colonies is shown in parenthesis. Bottom: Quantification of the transposition assay in HeLa cells. Error bars represent standard error (n=3).

FIG. 4 shows insertion sites as derived by sequence analysis of the neomycin locus from isolated neomycin positive HeLa cells. Insertions of SB IRs correctly occur at TA dinucleotides.

FIG. 5(a) shows the retention of hsSB delivered into HeLa cells as protein or expressed from plasmid DNA. Western blot analysis shows almost complete loss of delivered hsSB protein 48 hours after electroporation, whereas cells transfected with hsSB expression plasmids produce high level of protein continuously from 24 hours to 5 days after transfection. Western blot was performed on lysate from HeLa cells transfected with 0.5 µg of pSBTer (Tpn) and electroporated with 10 µg hsSB protein or transfected with 0.5 µg hsSB expression plasmid. Samples were taken at the indicated time points and 20 µg-s of the total lysate were separated by electrophoresis and transferred to a nitrocellulose membrane. The SB was detected with anti-SB antibody. The internal loading control was glyceraldehyde 3-phosphate dehydrogenase (GAPDH) detected with anti-GAPDH antibody. Measurement of the intensities of the bands allows to quantify hsSB persistence in HeLa cells over time (as shown in the chart on the left).

A Comparison of genetic engineering efficiency in HeLa cells as executed by hsSB provided on an expression plasmid or directly delivered as a protein by electroporation is shown in FIG. 5(b) to 5(e). As can be seen from the figures, genetic engineering efficiency does not depend on the transfection method, although protein electroporation is for a shorter time period more efficient, whereas plasmid transfection yields long term expression of the transposase.

A schematic representation of the SBprotAct engineering procedure with quantification by cell sorting is shown in FIG. 6. FIG. 7 shows a representative flow cytometric analysis of HeLa cells transfected with Venus-carrying transposon plasmid and electroporated with hsSB transposase. Venus-positive cells are identified 3 weeks post-transfection, so as to select for transposition positive cells. The electroporated hsSB protein amounts are indicated above each chart. Y axis: propidium iodide (PI) staining to select living cells. X-axis: green fluorescence from Venus. NT: non-transfected.

Example 3: Gene Delivery Using hsSB Transposase in CHO Cells and Mouse Embryonic Stem Cells (mESCs)

A representative flow cytometric analysis of Chinese Hamster Ovary (CHO) cells transfected with Venus-carrying transposon plasmid and electroporated with hsSB transposase is shown in FIG. 8. Venus-positive cells are identified 3 weeks post-transfection, so as to select for transposition positive cells. The electroporated hsSB protein amounts are indicated above each chart. Y axis: propidium iodide (PI) staining to select living cells. X-axis: green fluorescence from Venus. NT: non-transfected.

FIG. 9 shows genetic engineering of mESCs by direct delivery of the hsSB transposase protein. (a): Representative transposition assay in mouse embryonic stem cells (mESCs) demonstrating efficient transgene (neomycin resistance) insertions by the transfected hsSB transposase. (b): Representative flow cytometric analysis of mESCs transfected with Venus-carrying transposon plasmid and electroporated with hsSB transposase. Venus-positive cells are identified 3 weeks post-transfection, so as to select for transposition positive cells. The electroporated hsSB protein amounts are indicated above each chart. Y axis: propidium iodide (PI) staining to select living cells. X-axis: green fluorescence from Venus. NT: nontransfected. (c) Oct4 staining confirms that engineered mESCs retain their pluripotent state.

Transgenesis efficiency of the SBprotAct system in different cell lines is shown in FIG. 10 as quantified by flow cytometric analysis. Errors are indicated as standard deviation (n=2). FIG. 11. (a) shows a representative transposition assay in mouse embryonic stem cells (mESCs) demonstrating efficient transgene (neomycin) insertions by the transfected hsSB transposase. In (b) a representative flow cytometric analysis of mESCs transfected with Venus carrying transposon plasmid and electroporated with hsSB transposase is provided. Venus-positive cells are identified 3 weeks post-transfection, so as to select for transposition positive cells. The electroporated hsSB protein amounts are indicated above each chart. Y axis: propidium iodide (PI) staining for living cells. X-axis: green fluorescence from Venus. NT: nontransfected. In FIG. 11 (c) Oct4 staining confirms that engineered mESCs retain their pluripotent state.

In a further experiment the inventors sought to quantify transposition efficiency. Transgenesis efficiency of the SBprotAct system in different cell lines was quantified by flow cytometric analysis. Results are provided in FIG. 12, errors are indicated as standard deviation (n=2).

In conclusion, the novel transposase variant and transfection strategy (i.e. SBprotAct) establishes a new generation of the SB transposon system for cell engineering based on the use of purified transposase protein, which is unprecedented in itself to date. In standard SB-based applications, expression of the SB transposase is achieved either from an expression plasmid or from protein-encoding messenger RNA delivered into target cells. In ongoing clinical gene therapy trials, expression plasmids are exclusively used as sources of the SB transposase. In comparison to transposase gene delivery, direct hsSB protein delivery in SBprotAct provides:

a) Comparable transgenesis rates in diverse cell types.

b) No risks of transposase-gene or -promoter integration, circumventing uncontrolled long-term transposition and undesired transcriptional activation (of e.g. oncogenes) in the target cells.

c) No need for transcription and translation in the target cells. This expands the applicability of SB-mediated engineering to cells in which protein over-expression is difficult and/or compromises cell viability.

d) Fast cell engineering and rapid protein turnover, as hsSB protein is degraded within 48 h from delivery. Therefore hsSB protein acts in a hit-and-run fashion, minimizing off-target activities (see below).

e) Lower cytotoxicity, reduced risks of insertional mutagenesis and transgene remobilization due to limited temporal window of transposition.

f) Lower number of insertions per cell at the same transgenesis rate, minimizing genome perturbations.

g) Dose-dependent efficiency. By varying the concentration of the transfected hsSB protein, the number of positive clones can be tightly controlled.

h) Discrete and adjustable number of insertion events. hsSB-mediated engineering produces clones with discrete number of insertions per genome, which can be adjusted by varying the protein dose. In contrast, uncontrolled level and time of transposition from expression plasmids leads to heterogeneous, multicopy clones.

In addition, for CAR-T cell generation the use of mRNA has been explored as alternative source of SB transposase, but the instability of mRNA raises quality control issues that could hinder widespread use for therapy. hsSB protein delivery offers several advantages in comparison to mRNA delivery:

i) Independence from cellular translation efficiency and regulation.

j) Even tighter and more direct control of transposition efficiency, since the SB transposase immediately works after transfection without the need for translation.

k) The possibility to assess protein quality and activity in vitro prior to application (assays described in publication and shown in FIG. 1h herein). This is of particular relevance for quality control procedures in a commercial or clinical setting.

To date, delivery of active transposases for high-efficient mammalian cell engineering has been achieved only for the PiggyBac transposase, but required incorporation of the protein into lentiviral particles. Thus, SBprotAct provides for the first time a completely virus-free system for efficient delivery of a transposase protein in a medically relevant setting, avoiding all safety concerns and financial limitations connected to the use and the manufacture of viral vectors.

In summary, our invention, the SBprotAct system, opens up new possibilities to achieve maximal control of SB transposition in its genetic engineering applications, making SB an ever-safer genetic tool. Direct delivery of the hsSB protein allows rapid transposase clearance from the cell, avoiding the undesired effects of long-term transposition. Moreover, providing directly the active factor of transposition, the rates and time frame of active transgene insertion can be finely modulated and do not depend on the timeline and stochastic events in transposase expression (from plasmids) or translation (from mRNAs) by the cellular machinery, thereby also avoiding the fitness costs for the target cell.

Presently, SB is the only non-viral gene delivery tool currently used to manufacture CAR T-cells in clinical trials and it has already advanced quite far in clinical development. While preserving all advantages of the current SB system, including simplicity, ease and low cost, the SBprotAct of the invention provides a novel approach to overcome safety issues concerning the use of the current SB system in clinical applications.

The invention claimed is:

1. A transposase polypeptide, wherein the transposase polypeptide is a Sleeping Beauty (SB) transposase and comprises an amino acid sequence having at least 90% sequence identity to SEQ ID NO:2 but with at least one mutated amino acid residue at position 176 or position 212 of SEQ ID NO:2.

2. The transposase polypeptide according to claim 1, wherein the transposase polypeptide comprises a mutation at position 176 and a mutation at position 212 of SEQ ID NO:2.

3. The transposase polypeptide according to claim 1, wherein the at least one mutated amino acid residue is mutated into a serine residue.

4. The transposase polypeptide according to claim 1, wherein the amino acid sequence has at least 90% sequence identity to an amino acid sequence of SEQ ID NO: 1 or SEQ ID NO: 3 between residues 150 to 250.

5. A transposon system comprising (a) a transposon unit containing inverted terminal repeats (ITRs) or direct terminal repeats (DTRs) that flank a sequence of interest to be inserted into the genome of a target cell; and (b) a transposase polypeptide according to claim 1.

6. A pharmaceutical composition comprising a transposase polypeptide according to claim 1, together with a pharmaceutically acceptable carrier and/or excipient.

7. A kit comprising (a) a transposon unit containing inverted terminal repeats (ITRs) or DTRs that flank a sequence of interest to be inserted into the genome of a target cell; and (b) a transposase polypeptide according to claim 1.

8. The transposase polypeptide according to claim 2, wherein the transposase polypeptide comprises mutations C176S and I212S.

9. The transposase polypeptide according to claim 4, wherein the amino acid sequence has at least 90% sequence identity to the full-length sequence shown in SEQ ID NO: 1 or SEQ ID NO: 3.

* * * * *